US 7,759,510 B2
Jul. 20, 2010

(12) United States Patent
Kay et al.

(54) PLATINUM COMPLEXES AND METHODS OF USE

(75) Inventors: Heidi Kay, Springfield, VA (US); Jay W. Palmer, Sun City Center, FL (US); Joseph A. Stanko, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 12/506,913

(22) Filed: Jul. 21, 2009

(65) Prior Publication Data

US 2009/0285884 A1    Nov. 19, 2009

Related U.S. Application Data

(62) Division of application No. 10/918,769, filed on Aug. 13, 2004, now Pat. No. 7,566,798.

(60) Provisional application No. 60/525,295, filed on Nov. 25, 2003, provisional application No. 60/519,943, filed on Nov. 14, 2003, provisional application No. 60/515,580, filed on Oct. 30, 2003, provisional application No. 60/481,226, filed on Aug. 13, 2003.

(51) Int. Cl.
*C07F 15/00* (2006.01)
*A61K 31/28* (2006.01)

(52) U.S. Cl. ............................ 556/137; 549/3; 548/108; 546/10; 514/492

(58) Field of Classification Search ................. 556/137; 514/492; 546/10; 548/108; 549/3
See application file for complete search history.

(56) References Cited

U.S. PATENT DOCUMENTS

| | | | |
|---|---|---|---|
| 4,177,263 | A | 12/1979 | Rosenberg et al. |
| 5,849,790 | A | 12/1998 | Palmer et al. |
| 5,922,689 | A | 7/1999 | Shaw |
| 7,238,372 | B2 | 7/2007 | Turkson et al. |
| 2002/0035243 | A1 | 3/2002 | Imfeld et al. |
| 2002/0120100 | A1 | 8/2002 | Bonny |
| 2003/0032594 | A1 | 2/2003 | Bonny |
| 2004/0175369 | A1 | 9/2004 | Yu et al. |
| 2005/0074502 | A1 | 4/2005 | Turkson et al. |
| 2005/0288365 | A1 | 12/2005 | Kay et al. |

FOREIGN PATENT DOCUMENTS

| EP | 0328274 A1 | 8/1989 |
|---|---|---|
| EP | 0812852 A1 | 12/1997 |
| WO | WO 2005/023824 | 3/2005 |

OTHER PUBLICATIONS

Allen, A.D. and Baird, M.C. "trans-Dichlorobistriphenylphosphineplatinum(II)" *Chemistry & Industry*, 1965, 3:139, abstract only.

Burdge, J.R. et al. "Oxidation of platinum (II) bis(ethylenediamine) complexes with the oxides of nitrogen, NO and $NO_2$; a model for synthesis of platinum (IV) nitro compounds as potential antitumor agents" *Florida Scientist*, 1995, vol. 58, No. 3, pp. 274-285.

Cernjaev, I.I. "Nitro-trichloro-verbindungen [Pt $a_2$ $Cl_3$ $NO_2$] Isomerie I, II, III" *Izv. Plat*, 8, 1931, 55/71, 64 as quoted in Gmelin, Handbook of Inorganic Chemistry, Pt, vol. 63, Part D, pp. 558-560.

Chernyaev, I.I. et al. "Action of hydrochloric acid on the nitrodiamines of platinum(II)" *Zhurnal Neorganicheskoi Khimii*, 1965, 10(1):300-302, abstract only.

Chernyaev, I.I. et al. "Reaction of platinum(II) nitrodiamines with hydrochloric acid" *Zhurnal Neorganicheskoi Khimii*, 1966, 11(6):1365-1373, abstract only.

Chernyaev, I.I. and Leonova, T.N. "Complexes of platinum with 2,2'-dimethylhydrazine" *Zhurnal Neorganicheskoi Khimii*, 1969, 14(2):591-592, abstract only.

Kukushkin, Y.N. and Dkhara, S.C. "Effect of intrasphere acido groups on the redox potentials of systems consisting of platinum complexes" *Zhurnal Neorganicheskoi Khimii*, 1969, 14(10):2816-2819, abstract only.

Kukushkin, V.Y. and Tkachuk, V.M. "Reaction of platinum(ii) nitro complexes with phosphorus pentachloride" *Zhurnal Neorganicheskoi Khimii*, 1987, 32(12):3118-3119, abstract only.

Palmer, J.W. et al. "Oxidation of platinum(II) mono(ethylenediamine) complexes with the oxides of nitrogen, NO and $NO_2$; possible antitumor agents" *Florida Scientist*, 1995, vol. 58, No. 4. pp. 359-365.

Turkson, J. et al. "Inhibition of constitutive signal transducer and activator of transcription 3 activation by novel platinum complexes with potent antitumor activity" *Molecular Cancer Therapeutics*, 2004, 3(12):1533-1542.

Zheligovskaya, N.N. et al. "Platinum(IV) diamine dichloro complex conversions in solutions" *Vestnik Moskovskogo Universiteta, Seriya 2: Khimiya*, 1970, 11(1):32-37, abstract only.

Akira, S. "Roles of STAT3 Defined by Tissue-Specific Gene Targeting", *Oncogene*, 2000, pp. 2607-2611, vol. 19.

Ardizzoni, A. et al. "The Combination of Etoposide and Cisplatin in Non-Small-Cell Lung Cancer (NSCLC)", *Ann. Oncol.*, 1999, pp. S13-17, vol. 10.

Bowman, T. et al. "STATs in Oncogenesis", *Oncogene*, 2000, pp. 2474-2488, vol. 19.

Bowman, T. et al. "Stat3-Mediated Myc Expression is Required for Src Transformation and PDGF-Induced Mitogenesis", *Proc Natl. Acad. Sci. USA*, 2000, pp. 7319-7324, vol. 98, No. 3.

Bromberg, J. F. et al. "Transcriptionally Active Stat1 is Required for the Antiproliferative Effects of Both Interferon Alpha and Interferon Gamma", *Proc. Natl. Acad. Sci. USA*, 1996, pp. 7673-7678, vol. 93.

(Continued)

*Primary Examiner*—Porfirio Nazario Gonzalez
(74) *Attorney, Agent, or Firm*—Saliwanchik, Lloyd & Saliwanchik

(57) ABSTRACT

The subject invention concerns platinum complexes that exhibit antitumor cell and/or antiparasitic activity. The subject invention also concerns the use of platinum complexes of the invention to treat oncological and inflammatory disorders. The platinum complexes of the invention can also be used to treat or prevent infection by a virus or a bacterial or parasitic organism in vivo or in vitro.

17 Claims, 14 Drawing Sheets

OTHER PUBLICATIONS

Bromberg, J. F. et al. "Stat3 Activation is Required for Cellular Transformation by V-src", *Mol. Cell. Biol.*, 1998, pp. 2553-2558, vol. 18, No. 5.

Bromberg, J. F. et al. "Stat3 as an Oncogene", *Cell*, 1999, pp. 295-303, vol. 98.

Catlett-Falcone, R. et al. "Constitutive Activation of Stat3 Signaling Confers Resistance to Apoptosis in Human U266 Myeloma Cells", *Immunity*, 1999, pp. 105-115, vol. 10.

Catlett-Falcone, R. et al. "STAT Proteins as Novel Targets for Cancer Therapy", *Curr. Opin. Oncol.*, 1999, pp. 490-496, vol. 11.

Coffer, P. J. et al. "The Role of STATs in Myeloid Differentiation and Leukemia", *Oncogene*, 2000, pp. 2511-2522, vol. 19.

Darnell, J. E., Jr. et al. "Jak-STAT Pathways and Transcriptional Activation in Response to IFNs and Other Extracellular Signaling Proteins", *Science*, 1994, pp. 1415-1421, vol. 264, No. 5164.

Darnell, J. E., Jr. "STATs and Gene Regulation", *Science*, 1997, pp. 1630-1635, vol. 277.

Epling-Burnette, P. K. et al. "Inhibition of STAT3 Signaling Leads to Apoptosis of Leukemic Large Granular Lymphocytes and Decreased Mcl-1 Expression", *J. Clin. Invest*, 2001, pp. 351-361, vol. 107, No. 3.

Fukada, T. et al. "Two Signals are Necessary for Cell Proliferation Induced by a Cytokine Receptor gp130: Involvement of STAT3 in Anti-Apoptosis", *Immunity*, 1996, pp. 449-460, vol. 5.

Garcia, R. et al. "Constitutive Activation of Stat3 in Fibroblasts Transformed by Diverse Oncoproteins and in Breast Carcinoma Cells", *Cell Growth Diff.*, 1997, pp. 1267-1276, vol. 8.

Garcia, R. et al. "Activation of STAT Transcription Factors in Oncogenic Tyrosine Kinase Signaling", *J. Biomed. Sci.*, 1998, pp. 79-85, vol. 5.

Garcia, R. et al. "Constitutive Activation of Stat3 by the Src and JAK Tyrosine Kinases Participates in Growth Regulation of Human Breast Carcinoma Cells", *Oncogene*, 2001, pp. 2499-2513, vol. 20.

Gouilleux, F. et al. "Prolactin and Interleukin-2 Receptors in T Lymphocytes Signal Through a MGF-STAT5-like Transcription Factor", *Endocrinology*, 1995, pp. 5700-5708, vol. 136, No. 12.

Grandis, J. R. et al. "Requirement of Stat3 but Not Stat1 Activation for Epidermal Growth Factor Receptor-Mediated Cell Growth In Vitro", *J. Clin. Invest.*, 1998, pp. 1385-1392, vol. 102, No. 7.

Grandis, J. R. et al. "Constitutive Activation of Stat3 Signaling Abrogates Apoptosis in Squamous Cell Carcinogenesis In Vivo", *Proc. Natl. Acad. Sci. USA*, 2000, pp. 4227-4232, vol. 97, No. 8.

Grandis, J. R. et al. "Epidermal Growth Factor Receptor—Mediated Stat3 Signaling Blocks Apoptosis in Head and Neck Cancer", *Laryngoscope*, 2000, pp. 868-874, vol. 110.

Hirano, T. et al. "Roles of STAT3 in Mediating the Cell Growth, Differentiation and Survival Signals Relayed Through the IL-6 Family of Cytokine Receptors", *Oncogene*, 2000, pp. 2548-2556, vol. 19.

Horiguchi, A. et al. "STAT3, but Not ERKs, Mediates the IL-6-Induced Proliferation of Renal Cancer Cells, ACHN and 769P", *Kidney Int*, 2002, pp. 926-938, vol. 61.

Johnson, P. J. et al. "Overexpressed pp60$^{c\text{-}src}$ Can Induce Focus Formation Without Complete Transformation of NIH 3T3 Cells", *Mol. Cell. Biol.*, 1985, pp. 1073-1083, vol. 5, No. 5.

Kotenko, S. V. et al. "Jak-Stat Signal Transduction Pathway Through the Eyes of Cytokine Class II Receptor Complexes", *Oncogene*, 2000, pp. 2557-2565, vol. 19.

Kunisada, K. et al. "Activation of gp130 Transduces Hypertrophic Signals Via STAT3 in Cardiac Myocytes", *Circulation*, 1998, pp. 346-352, vol. 98.

Lin, T. S. et al. "STAT Signaling in the Pathogenesis and Treatment of Leukemias", *Oncogene*, 2000, pp. 2496-2504, vol. 19.

Nielsen, M. et al. "Constitutive Activation of a Slowly Migrating Isoform of Stat3 in Mycosis Fungoides: Tyrphostin AG490 Inhibits Stat3 Activation and Growth of Mycosis Fungoides Tumor Cell Lines", *Proc. Natl. Acad. Sci. USA*, 1997, pp. 6764-6769, vol. 94.

Nielsen, M. et al. "Inhibition of Constitutively Activated Stat3 Correlates with Altered Bcl-2/Bax Expression and Induction of Apoptosis in Mycosis Fungoides Tumor Cells", *Leukemia*, 1999, pp. 735-738, vol. 13.

Nitiss, J. L. "A Copper Connection to the Uptake of Platinum Anticancer Drugs", *Proc. Natl. Acad. Sci. USA*, 2002, pp. 13963-13965, vol. 99, No. 22.

Persons, D. L. et al. "Cisplatin-Induced Activation of Mitogen-Activated Protein Kinases in Ovarian Carcinoma Cells: Inhibition of Extracellular Signal-Regulated Kinase Activity Increases Sensitivity to Cisplatin", *Clin. Cancer Res.*, 1999, pp. 1007-1014, vol. 5.

Sanchez-Perez, I. et al. "Cisplatin Induces a Persistent Activation of JNK That is Related to Cell Death", *Oncogene*, 1998, pp. 533-540, vol. 16.

Schindler, C. et al. "Transcriptional Responses to Polypeptide Ligands: The JAK-STAT Pathway", *Annu. Rev. Biochem.*, 1995, pp. 621-651, vol. 64.

Seidel, H. M. et al. "Spacing of Palindromic Half Sites as a Determinant of Selective STAT (Signal Transducers and Activators of Transcription) DNA Binding and Transcriptional Activity", *Proc. Natl. Acad. Sci. USA*, 1995, pp. 3041-3045, vol. 92.

Smithgall, T. E. et al. "Control of Myeloid Differentiation and Survival by Stats", *Oncogene*, 2000, pp. 2612-2618, vol. 19.

Song, J. I. et al. "STAT Signaling in Head and Neck Cancer", *Oncogene*, 2000, pp. 2489-2495, vol. 19.

Stark, G. R. et al. "How Cells Respond to Interferons", *Annu. Rev. Biochem*, 1998, pp. 227-264, vol. 67.

Turkson, J. et al. "Stat3 Activation by Src Induces Specific Gene Regulation and is Required for Cell Transformation", *Mol. Cell. Biol.*, 1998, pp. 2545-2552, vol. 18, No. 5.

Turkson, J. et al. "Requirement for Ras/Rac1-Mediated p38 and c-Jun N-Terminal Kinase Signaling in Stat3 Transcriptional Activity Induced by the Src Oncoprotein", *Mol. Cell. Biol.*, 1999, pp. 7519-7528, vol. 19, No. 11.

Turkson, J. et al. "STAT Proteins: Novel Molecular Targets for Cancer Drug Discovery", *Oncogene*, 2000, pp. 6613-6626, vol. 19.

Turkson, J. et al. "Phosphotyrosyl Peptides Block Stat3-Mediated DNA Binding Activity, Gene Regulation, and Cell Transformation", *J. Biol. Chem.*, 2001, pp. 45443-45455, vol. 276, No. 48.

Wagner, B. J. et al. "The SIF Binding Element Confers sis/PDGF Inducibility Onto the c-fos Promoter", *EMBO J.*, 1990, pp. 4477-4484, vol. 9, No. 13.

Yu, C. L. et al. "Enhanced DNA-Binding Activity of a Stat3-Related Protein in Cells Transformed by the Src Oncoprotein", *Science*, 1995, pp. 81-83, vol. 269, No. 32.

Zhang, Y. et al. "Activation of Stat3 in v-Src-Transformed Fibroblasts Requires Cooperation of Jak1 Kinase Activity", *J. Biol. Chem.*, 2000, pp. 24935-24944, vol. 275.

Cuny, G.D. et al. "Photoactivated Virucidal Properties of Tridentate 2,2'-Dihydroxy Azobenzene and 2-Salicylideneaminophenol Platinum Pyridine Complexes", *Bioorganic & Medicinal Chemistry Letters*, 1999, pp. 237-240, vol. 9.

Toyoizumi, T. et al. "Combined Therapy with Chemotherapeutic Agents and Herpes Simplex Virus Type 1 ICP34.5 Mutant (HSV-1716) in Human Non-Small Cell Lung Cancer", 1999, *Human Gene Therapy*, pp. 3013-3029, vol. 10.

Samatov et al. Izvestiya Akademii Nauk SSSR Seriya Khimicheskaya, 1974, pp. 1467-1472, No. 9, XP009041872.

Chernyaev et al. Zhurnal Neorganicheskoi Khimii, 1966, pp. 1365-1373, vol. 11, XP009041845.

Muraveiskaya et al. Zhurnal Neorganicheskoi Khimii, 1971, pp. 1643-1649, vol. 16, XP009041849.

Rudyi et al. Koordinatsionnaya Khimiya, 1975, p. 1572, vol. 1, XP009041868.

Muravenskaya et al. Koordinatsionnaya Khimiya, 1975, pp. 779-790, vol. 1, XP009041867.

Le Postollec "Spectres de vibration et struture de composes de coordination nitres du platine IV" *Journal de La Chimie Physique et de Physico-Chime Biologique*, 1965, pp. 67-72, vol. 62, XP009041900.

Samatov et al. Izvestiya Akademii Nauk SSSR, Seriya Khimicheskaya, 1974, pp. 2142-2144, XP009041871.

Dickinson, W.L. and Johnson, R.C. "Mercuric ion induced hydrolysis of trans-dibromodinitroethylenediamineplatinum(IV)" *Inorganic Chem.*, 1973, 12(9):2048-2050.

Kortepeter, M.G. et al. "Managing potential laboratory exposure to Ebola virus by using a patient biocontainment care unit" *Emerging Infect. Dis.*, 2008, 14(6):881-887.

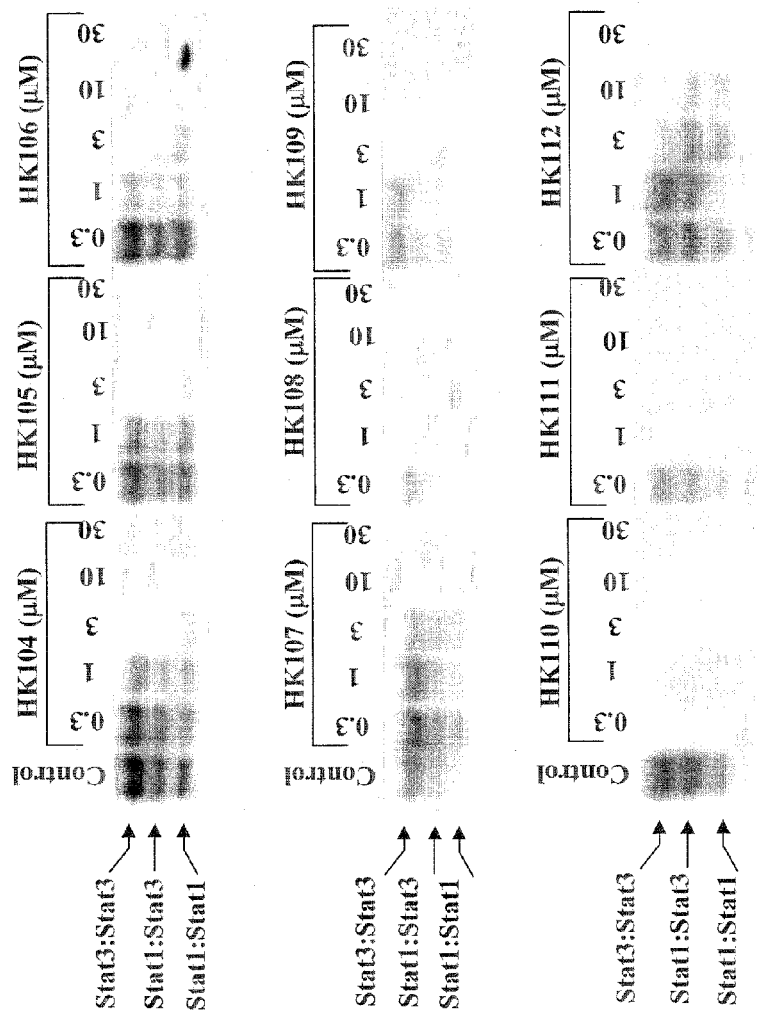
Fig. 12A -- EMSA analysis showing inhibition of STAT DNA-binding activity

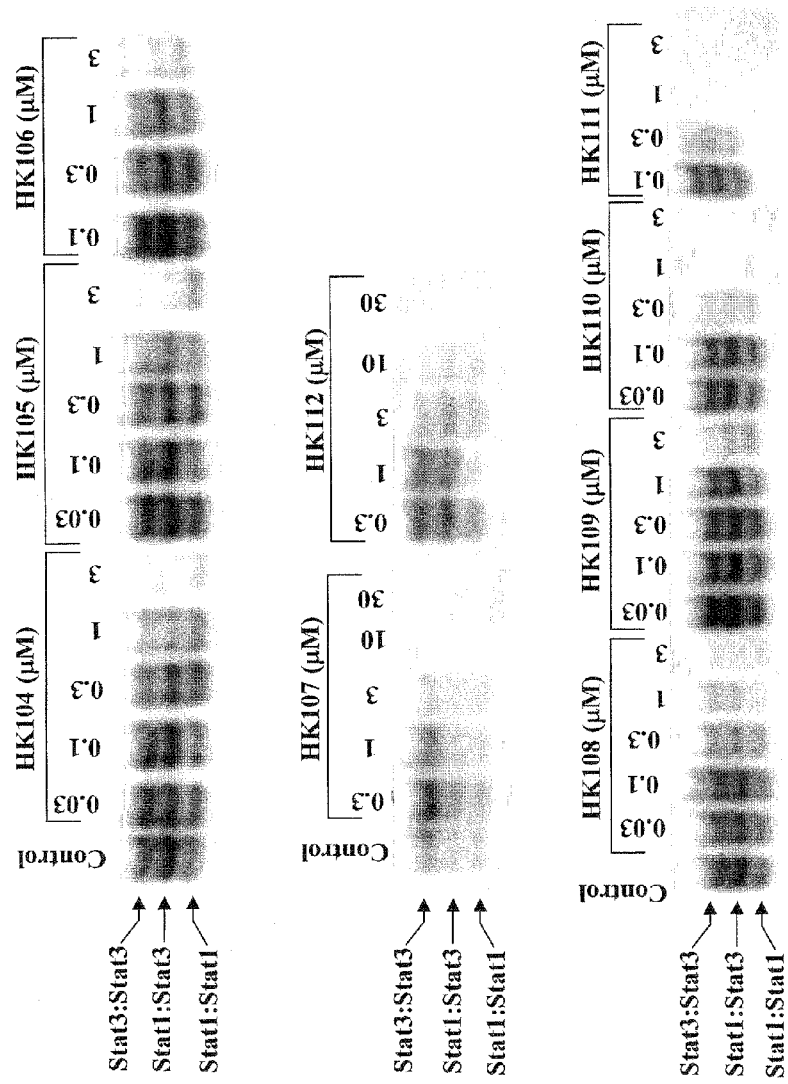
Fig. 12B—EMSA analysis showing inhibition of STAT DNA-binding activity

SEQUENCE LISTING

<160> NUMBER OF SEQ ID NOS: 1

<210> SEQ ID NO 1
<211> LENGTH: 24
<212> TYPE: DNA
<213> ORGANISM: Artificial sequence
<220> FEATURE:
<223> OTHER INFORMATION: oligonucleotide probe

<400> SEQUENCE: 1
agcttcattt cccgtaaatc ccta                      24

PLATINUM COMPLEXES AND METHODS OF USE

CROSS-REFERENCE TO RELATED APPLICATIONS

The present application is a divisional of U.S. application Ser. No. 10/918,769, filed Aug. 13, 2004, which claims the benefit of U.S. Provisional Application Ser. No. 60/481,226, filed Aug. 13, 2003, U.S. Provisional Application Ser. No. 60/515,580, filed Oct. 30, 2003, U.S. Provisional Application Ser. No. 60/525,295, filed Nov. 25, 2003, and U.S. Provisional Application Ser. No. 60/519,943, filed Nov. 14, 2003, the disclosure of each of which is incorporated herein by reference in its entirety.

BACKGROUND OF THE INVENTION

Cellular responses to growth factors and cytokines are characterized by activation of the Signal Transducer and Activator of Transcription (STAT) family of cytoplasmic transcription factors (Darnell, 1997; Darnell et al., 1994; Schindler et al., 1995; Stark et al., 1998; Smithgall et al., 2000; Akira, 2000; Hirano et al., 2000; Bromberg et al., 1996; Fukada et al., 1996; Kotenko et al, 2000). STATs are activated at a very early stage involving protein tyrosine kinase phosphorylation of tyrosine of growth factor receptors, receptor-associated Janus kinase (Jaks) or Src kinase families. This in turn induces phosphotyrosine (pTyr)-SH2 interactions between two STAT monomers in the formation of dimers, translocation to the nucleus, and binding to specific DNA response elements regulating gene expression essential for cell proliferation, differentiation, development and survival.

Normal STAT activation is tightly-regulated and has a short duration, which is in keeping with normal cellular requirements for mounting a response to external stimuli. However, persistent activation of specific STAT proteins, particularly Stat3 and Stat5, occurs with high frequency in some tumors and has a causal role in malignant transformation by promoting growth and survival of transformed and tumor cells, including those breast, prostate and head and neck squamous carcinoma cells, lymphomas and leukemias (Bromberg et al., 1999; Turkson et al., 1998; Bromberg et al., 1998; Catlett-Falcone et al., 1999a; Garcia et al., 2001; Grandis et al., 2000; Grandis et al., 1998; Nielsen et al., 1997; Nielsen et al., 1999; Epling-Burnette et al., 2001; reviewed in Bowman et al., 2000; Turkson et al., 2000; Song et al., 2000; Coffer et al., 2000; Lin et al., 2000; Catlett-Falcone et al., 1999b; Garcia et al., 1998). Of clinical importance, blockade of aberrant Stat3 signaling in malignant cells and whole tumors that contain them induces apoptosis and tumor regression.

Platinum complexes, the prototype of cisplatin (Cis-Pt), have been widely used as active anticancer agents (Ardizzoni et al., 1999; Nitiss, 2002) in a variety of human tumors, including testicular, ovarian, bladder carcinoma, head and neck, and non-small cell lung cancers. The outcome of treatments with cisplatin and other platinum-containing compounds is strongly linked to their alkylating effects on DNA. However, the potential impact of platinum-complex-based therapy on cellular signaling and the therapeutic importance of such interactions have yet to be explored. Reports show that cisplatin induces activation of members of the mitogen-activated protein kinase (MAPK) pathways (Persons et al., 1999; Sanchez-Perez et al., 1998), which may influence drug-induced apoptosis.

BRIEF SUMMARY OF THE INVENTION

The subject invention concerns platinum complexes and uses thereof. The platinum complexes of the invention can be used to treat oncological, viral, bacterial, and parasitic disease conditions.

BRIEF DESCRIPTION OF THE FIGURES

As shown in FIG. 5A, linear portions were measured at night (dark room) whereas reduction occurred in daytime. CPA-7 is not appreciably reduced by GSH but by light. As shown in FIG. 5B-C, scanning kinetics over two hours shows little change. Reduction is attributed to room light.

FIGS. 12A-B are photographs showing nuclear extracts containing activated Stat1 and Stat3 are treated with the indicated concentrations of other platinum (IV) complexes (designated herein as HK 104, HK 105, HK 106, HK 107, HK 108, HK 109, HK 110, HK 111, and HK 112) for 30 min at room temperature prior to incubation with radiolabeled hSIE oligonucleotide probe. Stat1 and Stat3 binding activities to hSIE probe are shown.

BRIEF DESCRIPTION OF THE SEQUENCE

Figure 1:
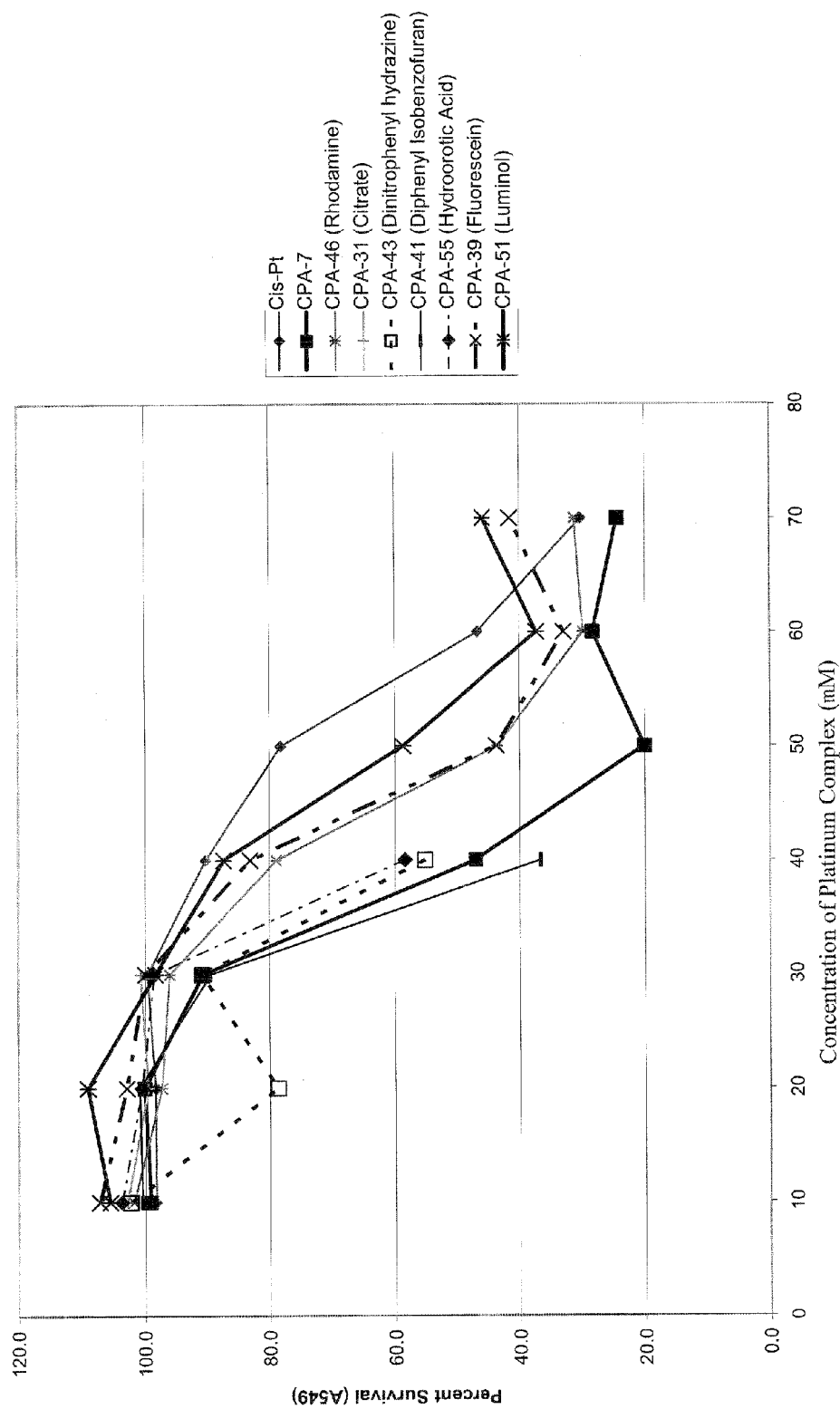
FIG. 1 shows the results in graph form from an MTT assay. Cisplatin is also designated as "Cis-Pt."

SEQ ID NO:1 is the nucleotide sequence of an oligonucleotide probe.

DETAILED DISCLOSURE OF THE INVENTION

The subject invention concerns platinum complexes and uses thereof. Platinum complexes of the invention can induce apoptosis and/or inhibit tumor cell growth and can also be used to treat cancers. The platinum complexes of the invention also can be used as antiviral, antibacterial, and antiparasitic agents. It has been suggested that cellular cytotoxicity of platinum (IV) compounds is a result of platinum (IV) compounds being reduced to platinum (II) in the cell. Surprisingly, platinum (IV) complexes of the present invention may not require this type of reduction in the cells to have a cytotoxic effect. Therefore, the platinum complexes of the present invention are distinct from platinum compounds in the art by maintaining their correct oxidative conformation as platinum (IV) compounds which are more effective than the existing platinum (II) compounds. In addition, platinum complexes of the invention can also form nitric oxide in the cells as radicals thereby killing the cells through the formation of oxide radicals.

Platinum complexes of the invention include those complexes having the structure shown in formula I:

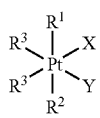
(I)

wherein

X and Y are, independently, any halogen, —NO$_2$, —ONO, or the structure:

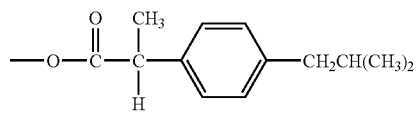

or X and Y together form the structure:

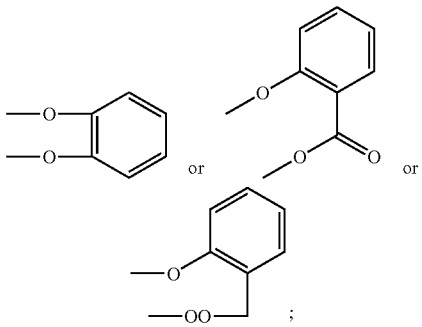

$R^1$ is —NO$_2$ or —ONO;

$R^2$ is any halogen, —OH, —ONO, —ONO$_2$, —COR$^{10}$, —OPO$_3$R$^{10}$R$^{11}$, —OSO$_3$H, —OSeOOH, —SeOOH, —AsO$_2$, —OAsO$_2$, —NR$^{10}$R$^{11}$, —NHR$^{10}$R$^{11}$, —OOCR$^{15}$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —NO$_2$, —NH$_2$, —N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, or the structure:

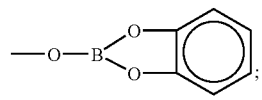

any of which can be substituted with any halogen, —NH$_2$, —COOH, —OH, alkoxy, cycloalkoxy;

$R^3$ is, independently, —NH$_3$, or —NHR$^7$;

$R^7$ is H, C$_{1-6}$ alkyl, alkoxy, or aryl, optionally substituted with —NO$_2$ or —COOH;

$R^{10}$ and $R^{11}$ are, independently, H, —NH$_2$, —OH, —NHR$^7$, CONHR$^7$, CON(R$^7$)$_2$, C$_{1-6}$ alkyl, aryl, or heteroaryl, any of which can be optionally substituted with any halogen, —COOH, —OH, —NO$_2$, —NH$_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{15}$ is alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —NO$_2$, —NH$_2$, —N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

or a pharmaceutically acceptable salt thereof.

In one embodiment, X and Y can be, independently, fluorine (F), chlorine (Cl), bromine (Br) or iodine (I). In an exemplified embodiment, X is Cl and Y is Cl.

In one embodiment, $R^1$ is —NO$_2$, $R^2$ is Cl and $R^3$ is —NH$_3$.

Platinum complexes of the invention can also have the structure shown in formula II:

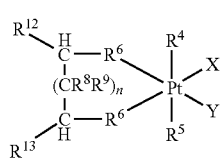
(II)

wherein

X and Y are, independently, any halogen, or the structure:

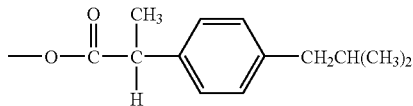

or X and Y together form the structure:

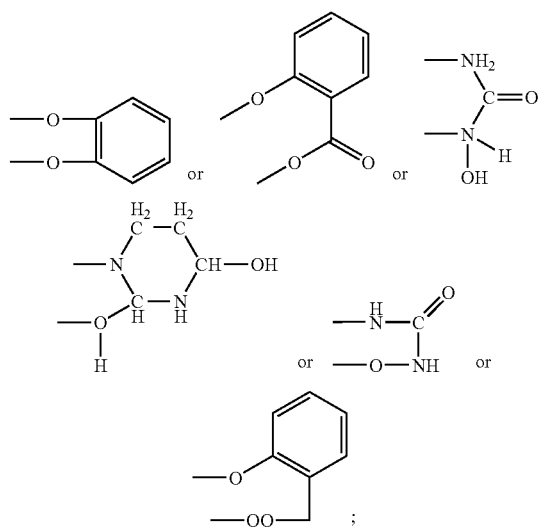

$R^4$ is —$NO_2$ or —ONO;

$R^5$ is any halogen, —OH, —ONO, —$ONO_2$, —$COR^{10}$, —$OPO_3R^{10}R^{11}$, —$OSO_3H$, —OSeOOH, SeOOH, —$AsO_2$, —$OAsO_2$, —$NR^{10}R^{11}$, —$NHR^{10}R^{11}$, —$OOCR^{15}$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —$NO_2$, —$NH_2$, —N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, or the structure:

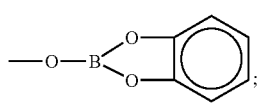

any of which can be substituted with any halogen, —$NH_2$, —COOH, —OH, or Y and $R^5$ form the structure:

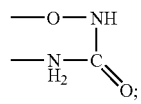

or X, Y, and $R^5$ together form the structure:

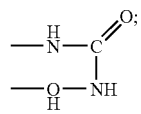

$R^6$ is, independently, $NH_2$ or NH;

$R^7$ is H, $C_{1-6}$ alkyl, alkoxy, aryl, optionally substituted with —$NO_2$ or —COOH;

$R^8$ and $R^9$ are, independently, H, $C_{1-6}$ alkyl, or —OH, any of which can be optionally substituted with any halogen, —COOH, —OH, —$NO_2$, —$NH_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; $R^{10}$ and $R^{11}$ are, independently, H, —$NH_2$, —OH, —$NHR^7$, $CONHR^7$, $CON(R^7)_2$, $C_{1-6}$ alkyl, aryl, or heteroaryl, any of which can be optionally substituted with any halogen, —COOH, —OH, —$NO_2$, —$NH_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{12}$ and $R^{13}$ are, independently, H or $C_{1-6}$ alkyl, or $R^{12}$ and $R^{13}$ together form an aryl, cycloalkyl, heterocycloalkyl, or heteroaryl, any of which can be optionally substituted with any halogen, —COOH, —OH, —$NO_2$, —$NH_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{15}$ is alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —$NO_2$, —$NH_2$, —N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

n is any integer from 0 to 6;

or a pharmaceutically acceptable salt thereof.

In one embodiment, X and Y can be, independently, fluorine (F), chlorine (Cl), bromine (Br) or iodine (I). In an exemplified embodiment, X is Cl and Y is Cl.

In one embodiment, $R^4$ is —$NO_2$, $R^5$ is Cl, $R^6$ is —$NH_2$, and n is 0.

Platinum complexes of the invention can also have the structure shown in formula III or IV:

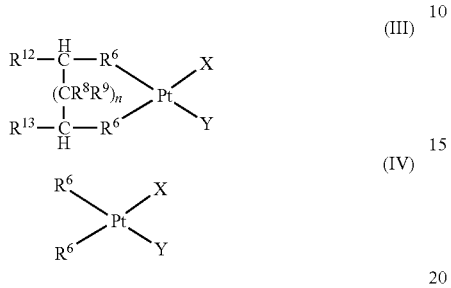

wherein

X and Y are, independently, any halogen, —$NO_2$, —ONO, or X and Y together form the structure:

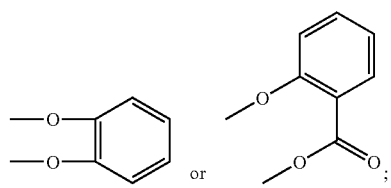

$R^6$ is, independently, $NO_2$, N, NH, or $NH_2$;

$R^8$ and $R^9$ are, independently, H, $C_{1-6}$ alkyl, or —OH, any of which can be optionally substituted with any halogen, —COOH, —OH, —$NO_2$, —$NH_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{12}$ and $R^{13}$ are, independently, H or $C_{1-6}$ alkyl, or $R^{12}$ and $R^{13}$ together form an aryl, cycloalkyl, heterocycloalkyl, or heteroaryl, any of which can be optionally substituted with any halogen, —COOH, —OH, —$NO_2$, —$NH_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

n is any integer from 0 to 6;

or a pharmaceutically acceptable salt thereof.

In one embodiment, X and Y can be, independently, fluorine (F), chlorine (Cl), bromine (Br) or iodine (I). In an exemplified embodiment, X is Cl and Y is Cl.

Also contemplated within the scope of the invention are platinum complexes that are not defined by formula I or formula II but that are specifically exemplified in the Table 5 presented herein. Exemplified embodiments of platinum complexes of the invention are shown in Table 5. The chemical structure of a complex along with a designation name (e.g., CPA-XX) is shown in the Table. Alternative designation names (e.g., HKXXX) of a complex are shown in parentheses.

Platinum complexes of the invention also include those complexes having the structure shown in formula V or formula VI:

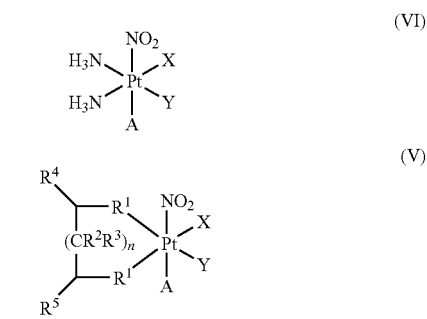

wherein

X and Y are, independently, any halogen, —OH, $H_2O$, or —$SO(CH_3)_2$; and A can be any of the following:

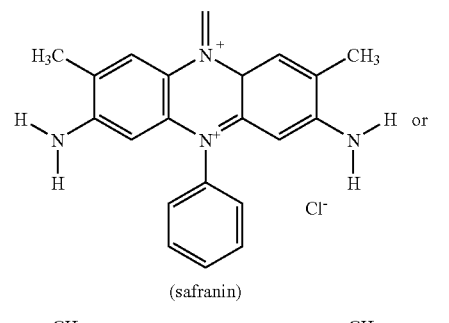

(safranin)

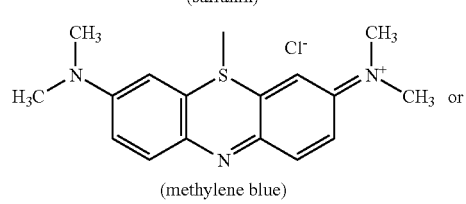

(methylene blue)

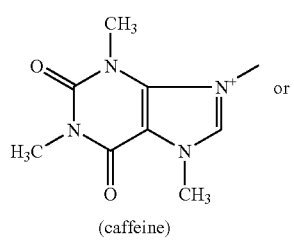

(caffeine)

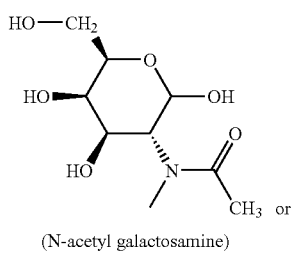

(N-acetyl galactosamine)

-continued
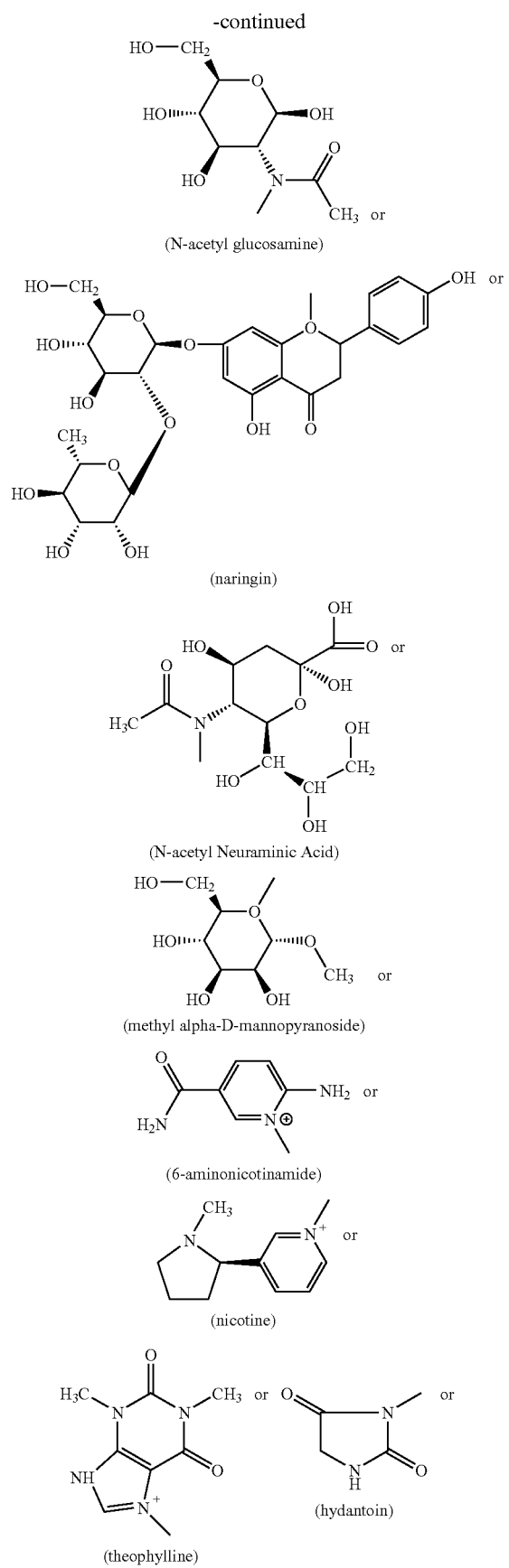
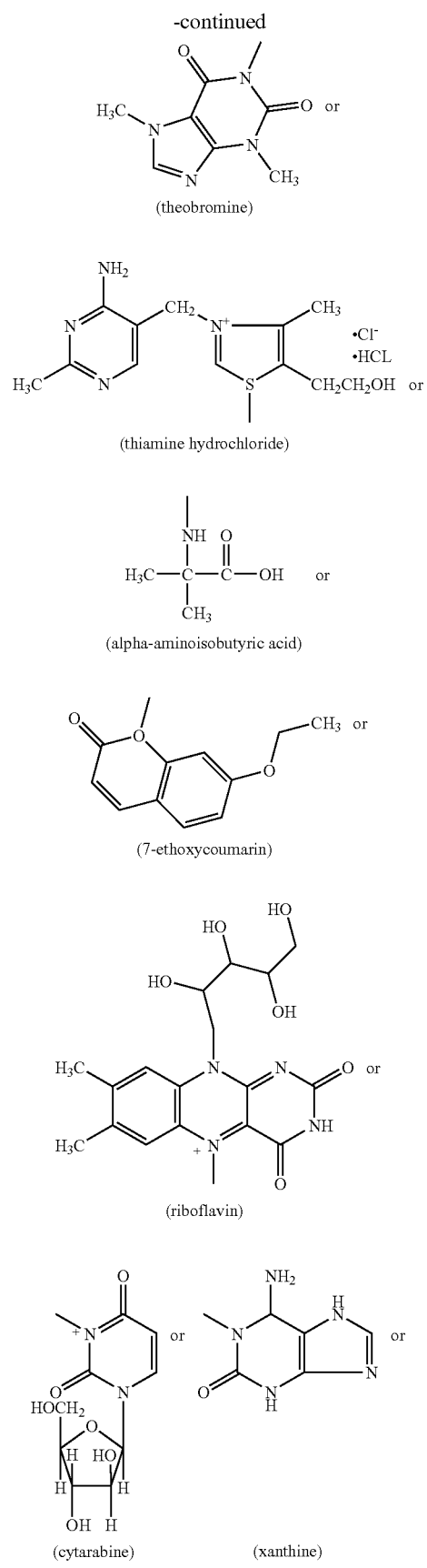

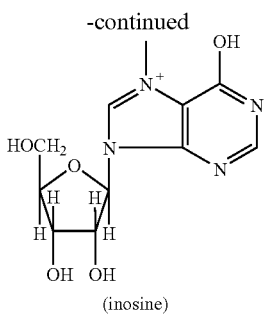
(inosine)

and wherein $R^1$ is, independently, $NH_2$ or NH;

$R^2$ and $R^3$ are, independently, H, —OH, $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, and heteroarylcarbonyl.

$R^4$ and $R^5$ are, independently, H or $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl or $R^4$ and $R^5$ together form a cycloalkyl, cycloalkoxy, aryl, aryloxy, heterocycloalkyl, heteroaryl, arylcarbonyl, and heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, and heteroarylcarbonyl;

n is any integer from 0 to 6;

or a pharmaceutically acceptable salt thereof.

In one embodiment, X and Y can be, independently, chlorine (Cl), bromine (Br) or iodine (I). In an exemplified embodiment, X is Cl and Y is Cl.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O-group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and spiro rings, containing from about six to about 14 carbon atoms. Aryloxy means an aryl-O-group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO-group in which the aryl group is as described herein. Heteroarylcarbonyl means a heteroaryl-CO-group in which the heteroaryl group is as described herein and heterocycloalkylcarbonyl means a heterocycloalkyl-CO-group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), Bromine (Br), and iodine (I).

The term pharmaceutically-acceptable salts means salts of the platinum complexes of the invention which are prepared with acids or bases, depending on the particular substituents present on the subject complexes described herein. Examples of a pharmaceutically-acceptable base addition salts include sodium, potassium, calcium, ammonium, or magnesium salt. Examples of pharmaceutically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Pharmaceutically-acceptable salts of platinum complexes of the invention can be prepared using conventional techniques.

It will be appreciated by those skilled in the art that certain of the platinum complexes of the invention may contain one or more asymmetrically substituted carbon atoms which can give rise to stereoisomers. All such stereoisomers, including enantiomers, and diastereoisomers and mixtures, including racemic mixtures thereof, are contemplated within the scope of the present invention.

Platinum complexes of the present invention are potent and selective disruptors of STAT activity. The complexes designated herein as CPA-7, CPA-10, CPA-39 (HK104), CPA-43 (HK106), CPA-46 (HK111), CPA-51 (HK110), CPA-55 (HK109), CPA-30 (HK112), and CPA-41 strongly disrupt Stat3 activity and interfere with its ability to bind to its consensus binding sequence. Platinum complexes of the invention can induce cell growth inhibition and apoptosis in transformed and tumor cells with persistently active STATs. Malignant cells with aberrant or constitutive STAT signaling are highly sensitive to platinum complexes of the invention. General cytotoxicity of the subject platinum complexes to normal cells is minimal or nil. In addition, strong apoptosis is induced by platinum compounds of the invention in malignant cells that harbor persistently-active STAT signaling, which correlates with suppression of aberrant STAT activity in these cells.

Platinum complexes of the invention also exhibit anti-tumor activity in melanoma and colon tumors in vivo. The abrogation of constitutively-active STATs in tumors treated with platinum complexes of the invention is consistent with their effects on STAT activity both in vitro and in whole cells, and together establish STAT-based anti-tumor effects of these compounds.

Methods of the invention comprise inhibiting function of a STAT by contacting a cell expressing a STAT with a platinum complex of the invention wherein the complex is taken in or otherwise provided inside the cell. Platinum complexes of the invention can physically interact with the DNA-binding domain of Stat3 and thereby disrupts its ability to bind to DNA. In Src-transformed mouse fibroblasts, as well as in human tumor cells of the breast, prostate, and mouse melanoma cells that contain constitutive Stat3 activity, both CPA-1 and CPA-7 abrogate Stat3 signaling function and thereby induce cell growth inhibition and apoptosis.

Methods of the invention also comprise inhibiting the function and/or growth and replication of a cell that is aberrantly or constitutively expressing a STAT, such as Stat1 or Stat3. In one embodiment, the method comprises contacting a cell with a platinum complex of the invention. In one embodiment, the cell is a tumor cell, cancer cell, or a transformed cell. The cell can be a cell from a mammal, including human, monkey, chimpanzee, ape, dog, cat, cow, pig, and horse.

Platinum complexes of the invention can be delivered to a cell either through direct contact with the cell or via a carrier means. Carrier means for delivering compositions to cells are known in the art and include, for example, encapsulating the composition in a liposome moiety. Another means for delivery of platinum complexes of the invention to a cell comprises attaching the platinum complexes to a protein or nucleic acid that is targeted for delivery to the target cell. Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery.

The subject invention also concerns methods for treating oncological or inflammatory disorders in a patient. In one embodiment, an effective amount of a platinum complex of the present invention is administered to a patient having an oncological or inflammatory disorder and who is in need of treatment thereof. Methods of the invention can optionally include identifying a patient who is or may be in need of treatment of an oncological or inflammatory disorder. The patient can be a human or other mammal, such as a primate (monkey, chimpanzee, ape, etc.), dog, cat, cow, pig, or horse, or other animals having an oncological disorder. Means for administering and formulating platinum complexes for administration to a patient are known in the art, examples of which are described herein. Oncological disorders include cancer and/or tumors of the bone, breast, kidney, mouth, larynx, esophagus, stomach, testis, cervix, head, neck, colon, ovary, lung, bladder, skin, liver, muscle, pancreas, prostate, blood cells (including lymphocytes), and brain. Inflammatory disorders include arthritis, multiple sclerosis, lupus, Crohn's disease, and related neurological and inflammatory connective tissue diseases (e.g., Sjögren's syndrome).

For the treatment of oncological disorders, the platinum complexes of this invention can be administered to a patient in need of treatment in combination with other antitumor or anticancer substances or with radiation therapy or with surgical treatment to remove a tumor. These other substances or radiation treatments may be given at the same as or at different times from the platinum complexes of this invention. For example, the platinum complexes of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The platinum complexes of the subject invention can be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The platinum complexes of the subject invention can also be used in combination with viral based treatments of oncologic disease. For example, platinum complexes of the invention can be used with mutant herpes simplex virus in the treatment of non-small cell lung cancer (Toyoizumi et al., 1999).

The subject invention also concerns methods for treating bacterial and viral infections of a patient using a platinum complex of the invention. In one embodiment, an effective amount of a platinum complex of the invention is administered to a patient having a bacterial or viral infection. Methods of the invention can optionally include identifying a patient who is or may be in need of treatment of a bacterial or viral infection. The patient can be a human or other mammal, such as a primate (monkey, chimpanzee, ape, etc.), dog, cat, cow, pig, or horse, or other animal infected with a bacteria or virus. Bacterial infections that can be treated according to the present invention include those from *Staphylococcus, Streptococcus, Salmonella, Bacillus, Clostridium, Pseudomonas, Neisseria, Mycobacterium,* and *Yersinia.* Viral infections that can be treated according to the present invention include, but are not limited to, those associated with human immunodeficiency virus (HIV), human T cell leukemia virus (HTLV), Papillomavirus (e.g., human papilloma virus), Polyomavirus (e.g., SV40, BK virus, DAR virus), orthopoxvirus (e.g., variola major virus (smallpox virus)), EBV, herpes simplex virus (HSV), hepatitis virus, Rhabdovirus (e.g., Ebola virus) and cytomegalovirus (CMV). Platinum compositions of the present invention can also be used to treat viral diseases in the presence of photodynamic therapy (Cuny et al., 1999). Platinum complexes of the present invention which can be used in photodynamic therapy include, but are not limited to, the complexes designated herein as CPA-30, CPA-32, CPA-38, CPA-39, CPA-41, CPA-42, CPA-43, CPA-45, CPA-46, CPA-51, CPA-53, CPA-54, CPA-55, and JP5. It is contemplated that these compounds are activated by light to activate their antiviral, antibacterial, antitumor, antiparasitic, or cellular effects.

Platinum complexes of the subject invention can also be used to treat patients infected with a parasitic organism. In one embodiment, the patient is administered a therapeutically effective amount of a platinum complex of the present invention. Methods of the invention can optionally include identifying a patient who is or may be in need of treatment of a parasitic infection. The patient can be a human or other mammal, such as a primate (monkey, chimpanzee, ape, etc.), dog, cat, cow, pig, or horse, or other animal infected with a parasitic organism. Disease conditions that can be treated according to the present invention include, but are not limited to, leishmania, toxoplasmosis, schistosomiasis, trypanosomiasis, pneumocystis, malaria, and trichinosis. Parasitic organisms that can cause disease conditions treatable according to the present invention include, but are not limited to, *Leishmania, Toxoplasma, Schistosoma, Plasmodium*, and *Trypanosoma*. The subject invention can also be used to treat gastrointestinal disorders caused by parasitic organisms such as, *Entamoeba, Giardia, Trichomonas*, and nematodes such as *Ascaris, Trichuris, Enterobius, Necator, Ancylostoma, Strongyloides*, and *Trichinella*. In another embodiment, a platinum complex of the present invention can be administered to patients prophylactically, wherein an uninfected patient is traveling to or will be present in an area where parasitic disease is prevalent or poses a risk to the patient. Accordingly, the patient can be treated with a composition of the present invention prior to the patient's exposure to or presence in the area where parasitic disease is prevalent or poses a risk and/or prior to infection with the parasitic organism.

Platinum complexes of the present invention can also be used to treat biological products in vitro that are contaminated with or suspected of being contaminated with a virus on a bacterial or parasitic organism. Biological products which can be treated with a platinum complexes of the present invention include, but are not limited to, whole blood, fractionated blood, plasma, serum, whole organs, or parts of organs, and cells, including blood cells, muscle cells, skin cells, and neural cells, and products derived from cells. Products derived from cells which can be treated with a platinum complex of the present invention include, but are not limited to, interferons, interleukins, blood clotting factors such as factor VIII, IX, X, and the like, insulin, polyclonal and monoclonal antibodies, growth factors, cytokines, and other products. Treatment of biological products comprises contacting the product for an effective amount of time and with an effective amount of a platinum complex of the present invention. If necessary, the biological product can be subsequently washed, preferably with a suitable sterile wash solution such as phosphate buffered saline, to remove the platinum complex that was used to treat the product.

Therapeutic application of the subject platinum complexes, and compositions containing them, can be accomplished by any suitable therapeutic method and technique presently or prospectively known to those skilled in the art. The subject platinum complexes can be administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject platinum complexes of the invention can be continuous or at distinct intervals as can be readily determined by a person skilled in the art.

Platinum complexes of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive platinum complex is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject platinum complexes include ethanol, dimethyl sulfoxide, glycerol, alumina, starch, and equivalent carriers and diluents. To provide for the administration of such dosages for the desired therapeutic treatment, pharmaceutical compositions of the invention will advantageously comprise between about 0.1% and 99%, and especially, 1 and 15% by weight of the total of one or more of the subject platinum complexes based on the weight of the total composition including carrier or diluent.

The platinum complexes of the subject invention can also be administered utilizing liposome technology, slow release capsules, implantable pumps, and biodegradable containers. These delivery methods can, advantageously, provide a uniform dosage over an extended period of time. The platinum complexes of the present invention can also be administered in their salt derivative forms or crystalline forms known to those of ordinary skill in the art.

The subject invention also concerns a packaged dosage formulation comprising in one or more containers at least one platinum compound of the subject invention formulated in a pharmaceutically acceptable dosage.

All patents, patent applications, provisional applications, and publications referred to or cited herein are incorporated by reference in their entirety, including all figures and tables, to the extent they are not inconsistent with the explicit teachings of this specification.

Materials and Methods

Synthesis of NitroPlatinum (IV) Complexes.

Cis-diammineoplatinum(II) dichloride (cisplatin) can be purchased at 99.9% purity from Sigma-Aldrich (#P4394). Using 0.300 grams of Cisplatin (0.00100 moles, FW=300.1), 150 mL of ultra deionized water and 50 mL of dichloroethane are added to a 250-mL Erlenmeyer flask. However, hexane or any organic solvents can be substituted in place of the dichlorethane used here. The choice of a sixth ligand includes the availability of a nitrogen, sulfur or oxygen atom in the chemical structure providing a Lewis base for bonding to the oxidized Pt. Other bondings are possible with metals, halides (such as HCl) or through chelation or interaction with pi molecular orbitals. One mole of the chosen ligand per mole of cisplatin should be weighed and added to the mixture. Organic solvents, such as dichloroethane, provide solubility for organic ligands of hydrophobic nature. A magnetic stir bar is placed in the mixture and the flask placed on a magnetic stir plate in a chemical fume hood. A lecture bottle of dinitrogen tetroxide is fitted with a regulator and Teflon hose, with a glass pipet attached to the hose outlet. The pipet tip is inserted into the lower solvent (e.g., dichloroethane) and the lecture bottle warmed slightly with a warm water bath. Nitrogen dioxide gas is released at a rate of approximately one bubble per second into the stirring mixture. The gas should be added until all the yellow cisplatin is consumed; the disappearance of yellow solids and yellow solution will indicate consumption of the available cisplatin. A blue color is noted to indicate formation of the nitrosyl intermediate; variations in hue and duration of this color have been observed. Gas addition is then terminated (remove the pipet to prevent vacuum suction into the lecture bottle) and the flask covered in aluminum foil to prevent light exposure. The flask should be left to stir overnight, uncovered.

Additional nitrogen dioxide may be added the next day to check for completeness of reaction. A blue color would indicate incomplete oxidation of platinum (II). Normally, this blue fades within ten minutes. For a colorless ligand, the solution has become yellow overnight. If blue color remains, allow it to continue stirring. The mixture requires air for complete oxidation, so should not be tightly covered. Continued oxidation with air can be accelerated using air blown through a trap into the Erlenmeyer, over the liquids. The solvents will evaporate in about two days, leaving a yellow precipitate, which is the product.

The precipitate can be purified via recrystallization in methanol, DMSO, or other suitable solvent. Alternatively, the product can be purified on silica columns or using HPLC.

MTT Assay.

1. Prepare a suspension of A549 cells at $2\times10^5$ cells per mL in supplemented DMEM/F12 growth medium.
2. Plate $2\times10^4$ cells per well in a 96 well cell culture plate by adding 100 µL of stock suspension to each well.
3. For each platinum compound (already in solution), prepare a readily usable stock solution in DMEM/F12 medium.
4. For each compound generate triplicate trials of 0, 10, 20, 30, 40, 50, 60, and 70 µM concentration. This is achieved in situ by adding appropriate volumes of stock solution to each well along with the volume of untreated medium necessary to generate the desired concentration in a final volume of 200 µL.
5. Gently agitate plates to mix contents. Incubate at 37° C., 7% $CO_2$ for 45 hours.
6. Add 20 µL of 5 mg/mL MTT solution (in PBS) to each well.
7. Gently agitate plates to mix contents and incubate an additional 3 hours to allow product development.
8. Remove plates from incubator and agitate to cause settling of formazan product.
9. Aspirate out liquid contents of each well using needle and syringe and discard.
10. Add 200 µL DMSO to each well to dissolve formazan product.
11. Agitate plates until all of the formazan product is in solution and no purple crystals remain on the bottom surface of the wells.
12. Read the absorbance of each well at 475 mm using Varian software for Cary 50 UV-vis Spectrophotometer with fiber optic probe accessory.

XTT Assay.

A 96-well plate was used for the assays. Approximately $2.5\times10^4$ cells in log phase were added to each well. A platinum complex of the invention was dispensed into each well (dissolved in 20% DMSO and 80% media), with additional media added as needed to account for uniform volumes. Control wells contained only cells and media. Each concentration assay was performed in triplicate. Plates were incubated for 48 hours at 37° C. with 7.5% $CO_2$. XTT from MD Biosciences. Quebec, was then added according to the provided protocol concentrations and allowed to react for 3 hours. Plates were agitated 5 minutes before reading absorbance at 475 nm on a Varian Cary 50 spectrophotometer with a fibreoptic probe. Percent survival as compared to control wells was plotted against platinum complex concentration.

Nuclear Extract Preparation and Analysis by EMSA of HK-Designated Platinum Complexes.

Nuclear extracts were prepared from NIH3T3/hEGFR cell that overexpress human epidermal growth factor (EGF) receptor and stimulated with EGF (6 ng/ml) for 15 min. Nuclear extracts were pre-incubated with compounds for 30 min at room temperature prior to incubation with radiolabeled probe. The $^{32}P$-labeled oligonucleotide probe used is hSIE (high affinity sis-inducible element, m67 variant, 5'-AGCTTCATTTCCCGTAAATCCCTA-3') (SEQ ID NO:1) that binds both Stat1 and Stat3.

Following are examples which illustrate procedures for practicing the invention. These examples should not be construed as limiting. All percentages are by weight and all solvent mixture proportions are by volume unless otherwise noted.

Example 1

MTT Assay Data for Platinum Complexes

Figure 2:
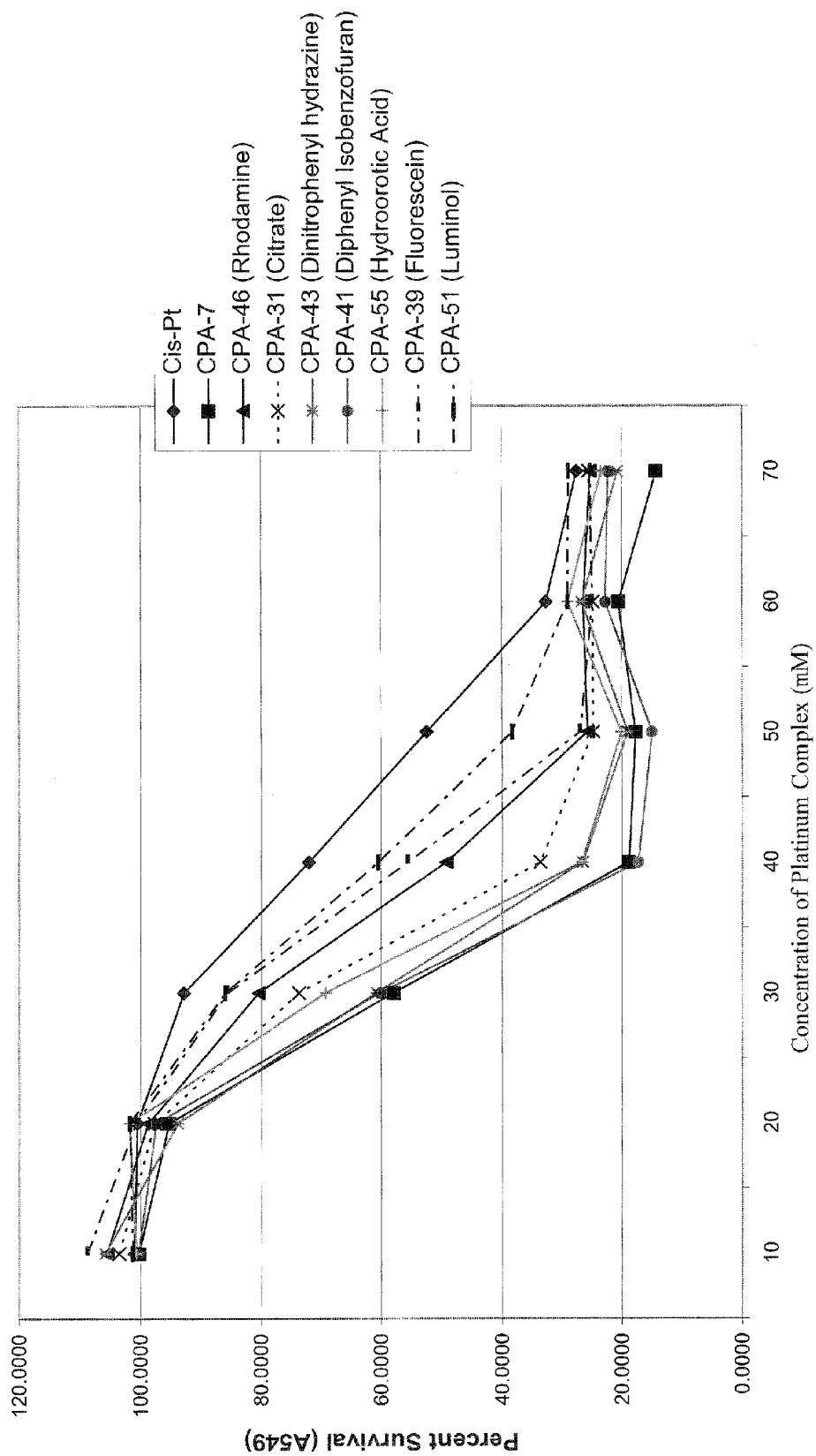
FIG. 2 shows the results in graph form from an MTT assay. Cisplatin is also designated as "Cis-Pt."
Figure 4:
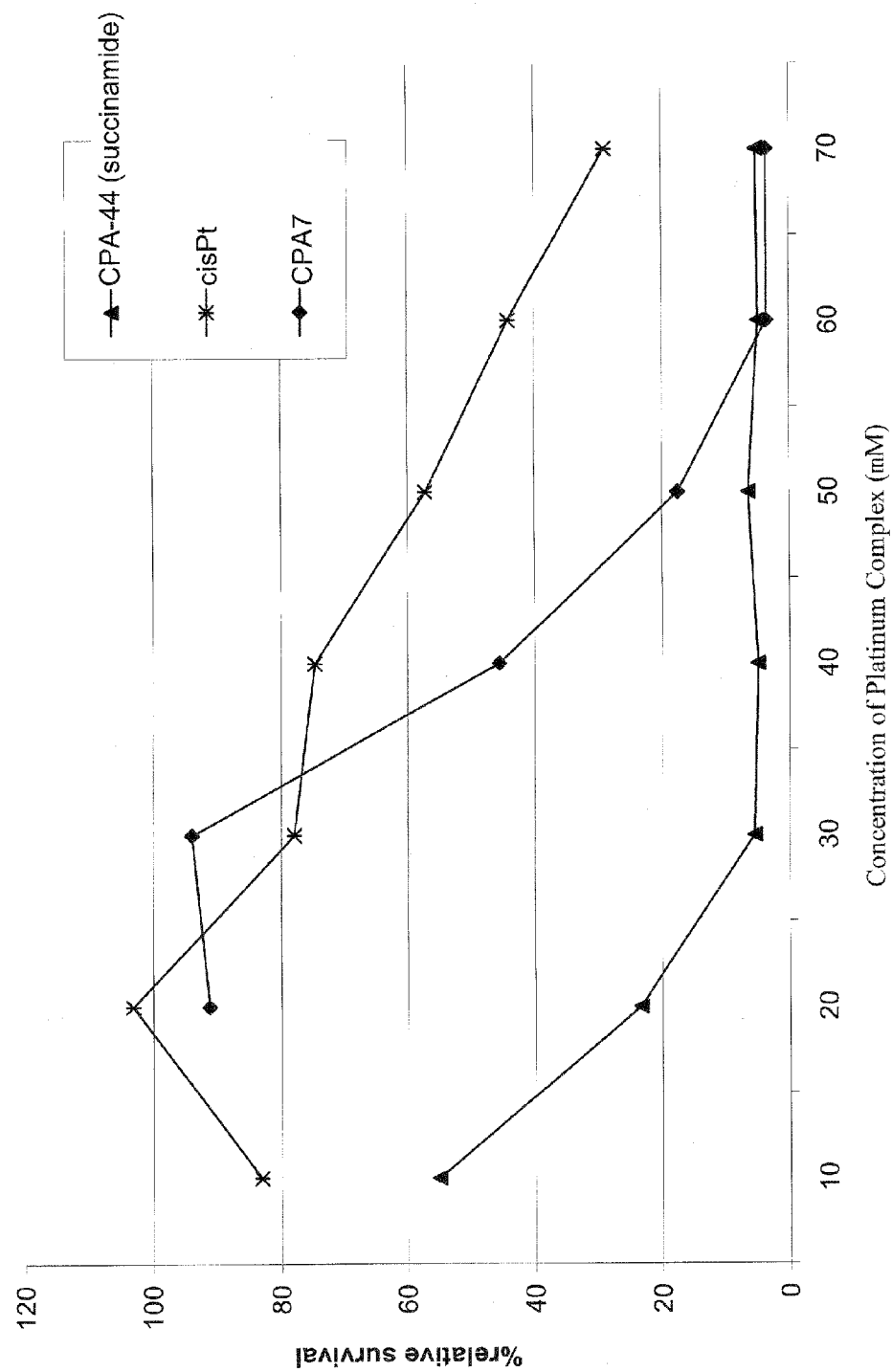
FIG. 4 shows the results in graph form from an MTT assay. Cisplatin is also designated as "Cis-Pt."
Figure 6:
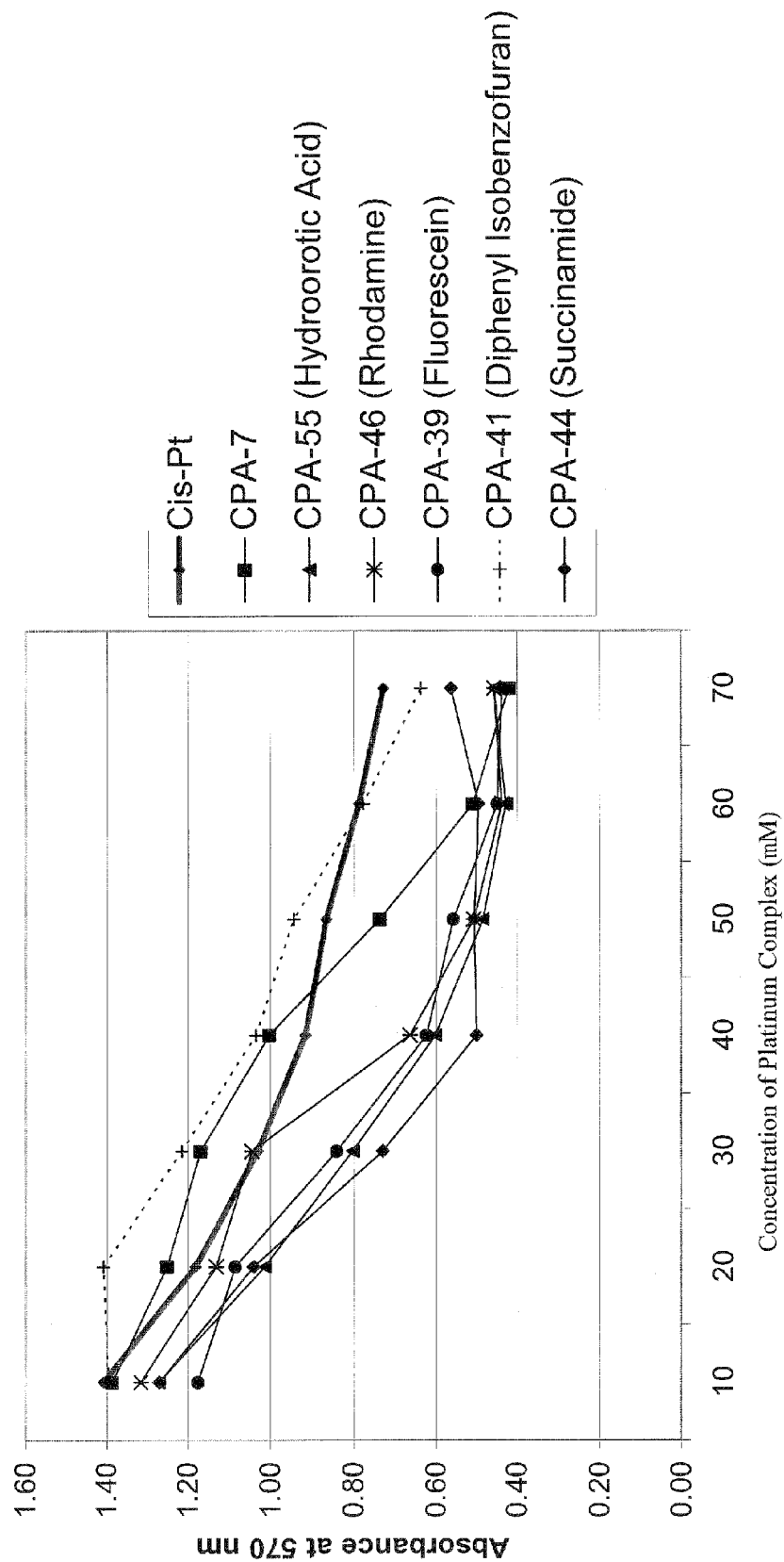
FIG. 6 shows the results in graph form from an MTT assay. Cisplatin is also designated as "Cis-Pt."

MTT assays are used for the quantitative determination of cellular proliferation and activation and for the quantitation of in vitro tumor cell sensitivity to anti-cancer compounds. The assay is based on the cleavage of the yellow tetrazolium salt MTT into purple colored formazan by metabolically active cells. Solubilized formazan product can be photometrically quantitated using an ELISA plate reader. A decrease in the number of living cells results in a decrease in total metabolic activity which leads to a decrease in color formation. Platinum complexes of the present invention were tested in MTT assays using A549 cells to determine anti-cancer cell activity. The results are shown in Tables 1, 2, 3, and 4 and FIGS. 1, 2 and 4. Table 1 shows percent survival of A549 cells and Table 2 shows the IC50 from the data in Table 1. FIGS. 1, 2, and 4 show percent survival versus platinum complex concentration in graphical form. FIG. 6 shows a graph of absorbance at 570 nm versus concentration of several platinum complexes (µm) of the invention.

TABLE 1

Percent of Survival of A549 Using Platinum Complex in MTT Assay

| Complex | Concentration (in μM) | Percent Survival | Average Absorbance |
|---|---|---|---|
| Cis-Pt | 10 | 98.2423 | 2.3196 |
|  | 20 | 98.3779 | 2.3228 |
|  | 30 | 99.6400 | 2.3526 |
|  | 40 | 90.2757 | 2.1315 |
|  | 50 | 78.1288 | 1.8447 |
|  | 60 | 46.7536 | 1.1039 |
|  | 70 | 30.1470 | 0.7118 |
| CPA-7 | 10 | 99.1021 | 2.3399 |
|  | 20 | 100.0974 | 2.3634 |
|  | 30 | 90.6908 | 2.1413 |
|  | 40 | 46.9993 | 1.1097 |
|  | 50 | 20.0712 | 0.4739 |
|  | 60 | 28.2750 | 0.6676 |
|  | 70 | 24.3742 | 0.5755 |
| CPA-46 (Rhodamine) | 10 | 101.7831 | 2.4032 |
|  | 20 | 97.3190 | 2.2978 |
|  | 30 | 96.0188 | 2.2671 |
|  | 40 | 78.8531 | 1.8618 |
|  | 50 | 43.5602 | 1.0285 |
|  | 60 | 29.8208 | 0.7041 |
| CPA-31 (Citrate) | 10 | 102.8080 | 2.4274 |
|  | 20 | 99.5087 | 2.3495 |
|  | 30 | 100.7073 | 2.3778 |
|  | 40 |  |  |
|  | 50 | not | performed |
|  | 60 |  |  |
|  | 70 |  |  |
| CPA-43 (Dinitrophenyl Hydrazine) | 10 | 102.2828 | 2.4150 |
|  | 20 | 78.5820 | 1.8554 |
|  | 30 | 90.8517 | 2.1451 |
|  | 40 | 55.1861 | 1.3030 |
|  | 50 |  |  |
|  | 60 | not | performed |
|  | 70 |  |  |
| CPA-41 (Diphenyl Isobenzofuran) | 10 | 100.4024 | 2.3706 |
|  | 20 | 100.9148 | 2.3827 |
|  | 30 | 89.4668 | 2.1124 |
|  | 40 | 36.6270 | 0.8648 |
|  | 50 |  |  |
|  | 60 | not | performed |
|  | 70 |  |  |
| CPA-55 (Hydroorotic Acid) | 10 | 103.6847 | 2.4481 |
|  | 20 | 100.5082 | 2.3731 |
|  | 30 | 98.5473 | 2.3268 |
|  | 40 | 58.3626 | 1.3780 |
|  | 50 |  |  |
|  | 60 | not | performed |
|  | 70 |  |  |
| CPA-39 (Fluorescein) | 10 | 107.2085 | 2.5313 |
|  | 20 | 102.9478 | 2.4307 |
|  | 30 | 99.9492 | 2.3599 |
|  | 40 | 83.0587 | 1.9611 |
|  | 50 | 43.7000 | 1.0318 |
|  | 60 | 32.9338 | 0.7776 |
|  | 70 | 41.4976 | 0.9798 |
| CPA-51 (Luminol) | 10 | 105.5652 | 2.4925 |
|  | 20 | 109.1017 | 2.5760 |
|  | 30 | 98.3186 | 2.3214 |
|  | 40 | 87.3152 | 2.0616 |
|  | 50 | 58.7396 | 1.3869 |
|  | 60 | 37.3004 | 0.8807 |
|  | 70 | 45.8219 | 1.0819 |

TABLE 2

Calculated IC50's from MTT Assay Data of Table 1

| Complex | Calculated IC 50 (uM concentration) |  |
|---|---|---|
| Cisplatin | 63.29 |  |
| CPA-51 (Luminol) | 61.21 |  |
| CPA-39 (Fluorescein) | 56.39 |  |
| CPA-46 (Rhodamine) | 52.88 |  |
| CPA-55 (Hydroorotic Acid) | 54.20 | Extrapolated from data 10-40 uM |
| CPA-43 (DNP) | 49.59 | Extrapolated from data 10-40 uM |
| CPA-41 (IBF) | 40.71 | Extrapolated from data 10-40 uM |
| CPA-7 | 45.43 |  |
| CPA-31 (Citrate) | 505.81 | Suspected error due to incomplete data set |

Values in bold are outside the measured range. All values are determined using a linear trend from percent survival vs. concentration data.

TABLE 3

Percent of Survival of A549 Using Platinum Complex in MTT Assay

| Complex | Concentration (in μM) | Percent Survival | Average Absorbance |
|---|---|---|---|
| Cis-Pt | 10 | 100.9661 | 2.4665 |
|  | 20 | 100.5199 | 2.4556 |
|  | 30 | 92.8650 | 2.2686 |
|  | 40 | 71.9432 | 1.7575 |
|  | 50 | 52.5114 | 1.2828 |
|  | 60 | 32.6293 | 0.7971 |
|  | 70 | 27.5001 | 0.6718 |
| CPA-7 | 10 | 100.1965 | 2.4477 |
|  | 20 | 95.3703 | 2.3298 |
|  | 30 | 57.9148 | 1.4148 |
|  | 40 | 18.7646 | 0.4584 |
|  | 50 | 17.6880 | 0.4321 |
|  | 60 | 20.5166 | 0.5012 |
|  | 70 | 14.2454 | 0.3480 |
| CPA-46 (Rhodamine) | 10 | 105.5017 | 2.5773 |
|  | 20 | 98.7269 | 2.4118 |
|  | 30 | 80.3840 | 1.9637 |
|  | 40 | 49.3021 | 1.2044 |
|  | 50 | 25.7153 | 0.6282 |
|  | 60 | 26.3867 | 0.6446 |
|  | 70 | 25.2364 | 0.6165 |
| CPA-31 (Citrate) | 10 | 103.5409 | 2.5294 |
|  | 20 | 97.7322 | 2.3875 |
|  | 30 | 73.5929 | 1.7978 |
|  | 40 | 33.5503 | 0.8196 |
|  | 50 | 24.7616 | 0.6049 |
|  | 60 | 24.8352 | 0.6067 |
|  | 70 | 25.4943 | 0.6228 |
| CPA-43 (Dinitrophenyl Hydrazine) | 10 | 105.7759 | 2.5840 |
|  | 20 | 93.8311 | 2.2922 |
|  | 30 | 60.7188 | 1.4833 |
|  | 40 | 26.5218 | 0.6479 |
|  | 50 | 18.9979 | 0.4641 |
|  | 60 | 26.6241 | 0.6504 |
|  | 70 | 20.7090 | 0.5059 |
| CPA-41 (Diphenyl Isobenzofuran) | 10 | 100.2906 | 2.4500 |
|  | 20 | 97.4457 | 2.3805 |
|  | 30 | 60.1171 | 1.4686 |
|  | 40 | 17.2336 | 0.4210 |
|  | 50 | 14.9290 | 0.3647 |
|  | 60 | 22.7148 | 0.5549 |
|  | 70 | 22.2891 | 0.5445 |
| CPA-55 (Hydroorotic Acid) | 10 | 100.6468 | 2.4587 |
|  | 20 | 101.8257 | 2.4875 |
|  | 30 | 69.1883 | 1.6902 |
|  | 40 | 26.6200 | 0.6503 |
|  | 50 | 20.0336 | 0.4894 |
|  | 60 | 28.9901 | 0.7082 |
|  | 70 | 23.4680 | 0.5733 |
| CPA-39 (Fluorescein) | 10 | 108.7069 | 2.6556 |
|  | 20 | 100.7655 | 2.4616 |

TABLE 3-continued

Percent of Survival of A549 Using Platinum Complex in MTT Assay

| Complex | Concentration (in μM) | Percent Survival | Average Absorbance |
|---|---|---|---|
| | 30 | 85.5295 | 2.0894 |
| | 40 | 55.5405 | 1.3568 |
| | 50 | 26.8779 | 0.6566 |
| | 60 | 24.9130 | 0.6086 |
| | 70 | 25.2405 | 0.6166 |
| CPA-51 (Luminol) | 10 | 101.2895 | 2.4744 |
| | 20 | 101.7970 | 2.4868 |
| | 30 | 85.9552 | 2.0998 |
| | 40 | 60.4118 | 1.4758 |
| | 50 | 38.2824 | 0.9352 |
| | 60 | 28.9983 | 0.7084 |
| | 70 | 28.8919 | 0.7058 |

TABLE 4

Percent of Survival of A549 Using Platinum Complex in MTT Assay

| Complex | Concentration (in μM) | Percent Survival | Average Absorbance |
|---|---|---|---|
| Cis-Pt | 10 | 83.09927847 | 0.5299 |
| | 20 | 103.1095973 | 0.6575 |
| | 30 | 77.94510544 | 0.497033333 |
| | 40 | 74.69369001 | 0.4763 |
| | 50 | 57.14022853 | 0.364366667 |
| | 60 | 44.12933942 | 0.2814 |
| | 70 | 29.06932676 | 0.185366667 |
| CPA-7 | 10 | | |
| | 20 | 91.22258971 | 0.5817 |
| | 30 | 93.97740632 | 0.599266667 |
| | 40 | 45.5459529 | 0.290433333 |
| | 50 | 17.51164263 | 0.111666667 |
| | 60 | 3.538920018 | 0.022566667 |
| | 70 | 3.538920018 | 0.022566667 |
| CPA-44 (Succinamide) | 10 | 54.96042107 | 0.350466667 |
| | 20 | 23.37150871 | 0.149033333 |
| | 30 | 5.493951165 | 0.035033333 |
| | 40 | 4.929396716 | 0.031433333 |
| | 50 | 6.424420535 | 0.040966667 |
| | 60 | 4.8718958 | 0.031066667 |
| | 70 | 5.164627736 | 0.032933333 |

TABLE 5

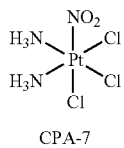

CPA-7

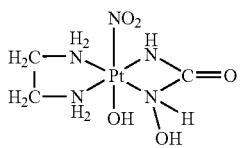

CPA-8

TABLE 5-continued

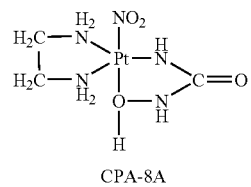

CPA-8A

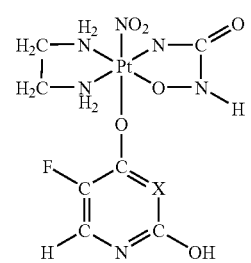

CPA-9

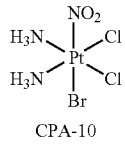

CPA-10

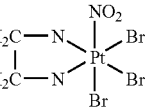

CPA-11

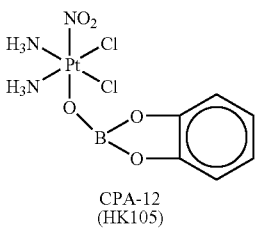

CPA-12
(HK105)

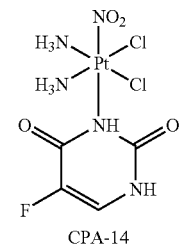

CPA-14

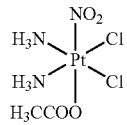

CPA-15

TABLE 5-continued

CPA-16, CPA-17, CPA-18, CPA-19, CPA-20, CPA-26, CPA-28, CPA-29

CPA-30 (HK112), CPA-31, CPA-32, CPA-33 (HK108), CPA-34, CPA-35

TABLE 5-continued
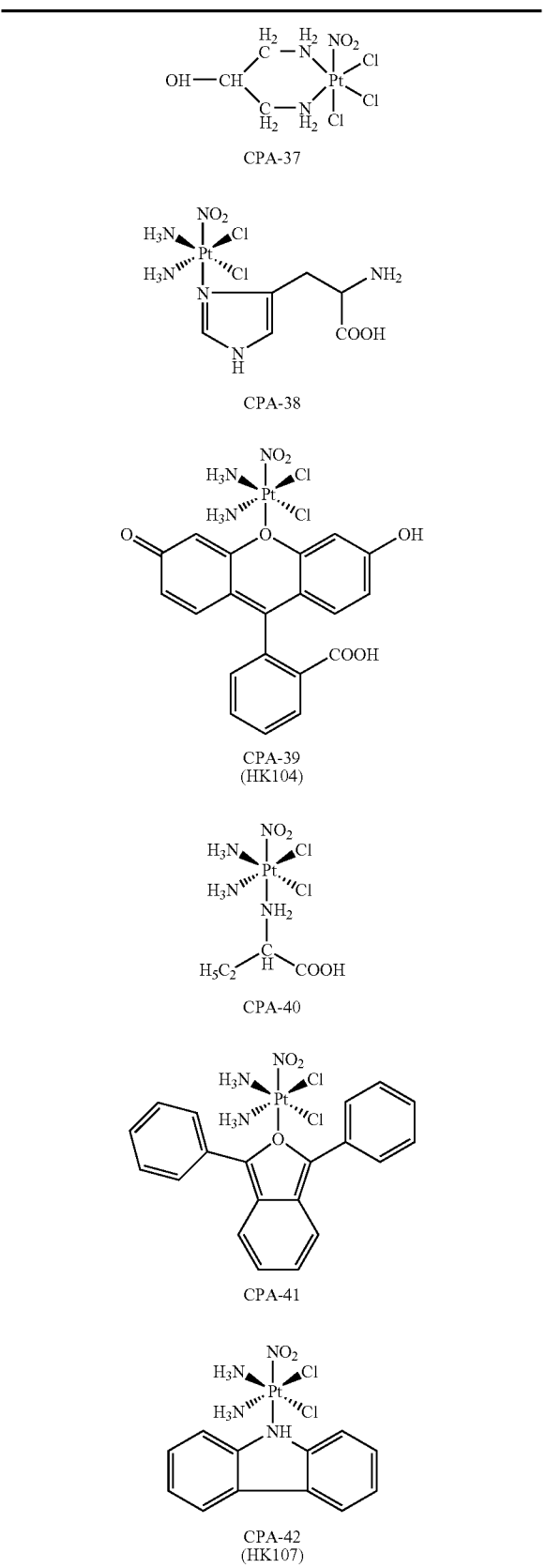
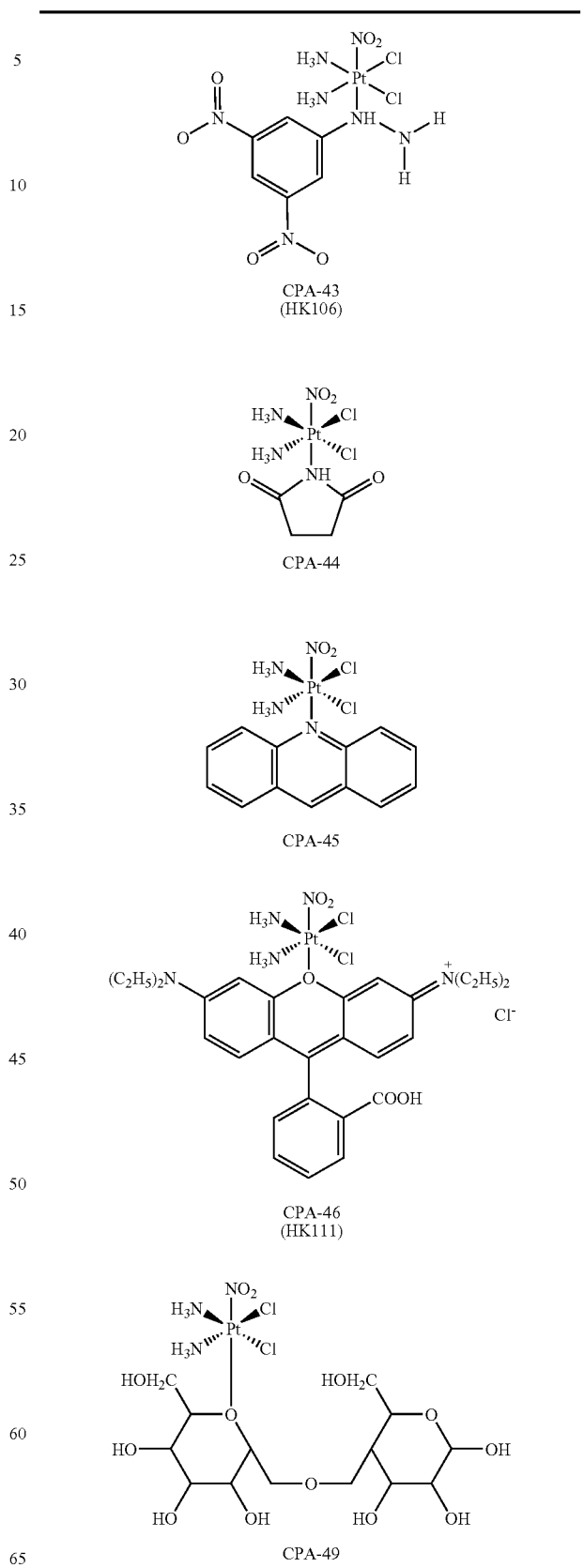

TABLE 5-continued

CPA-50

CPA-51
(HK110)

CPA-53

CPA-54

CPA-55
(HK109)

CPA-56

CPA-57

JP4

JP5

JP6A

JP6B

TABLE 5-continued

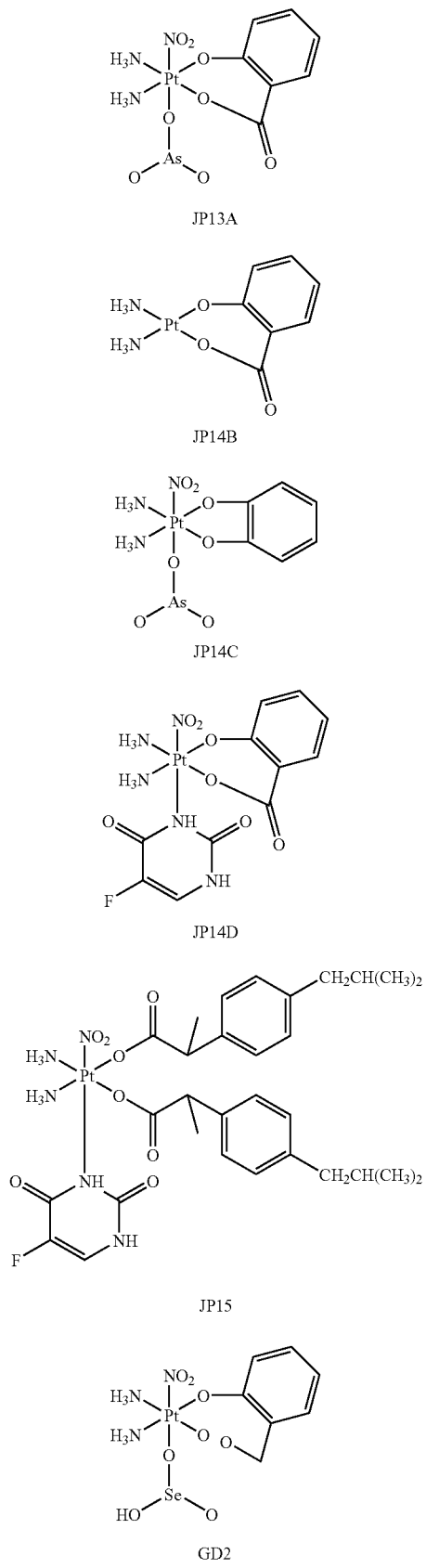

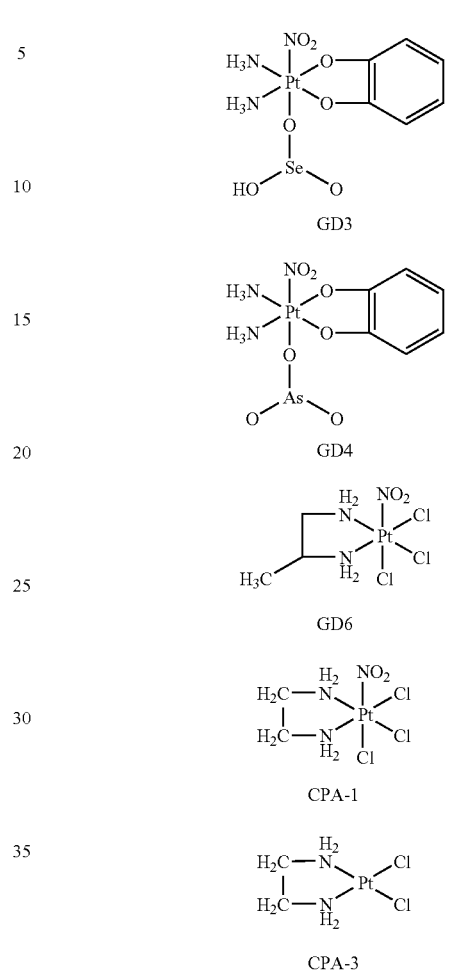

Example 2

XTT Assay Data for Platinum Complexes

Figure 3:
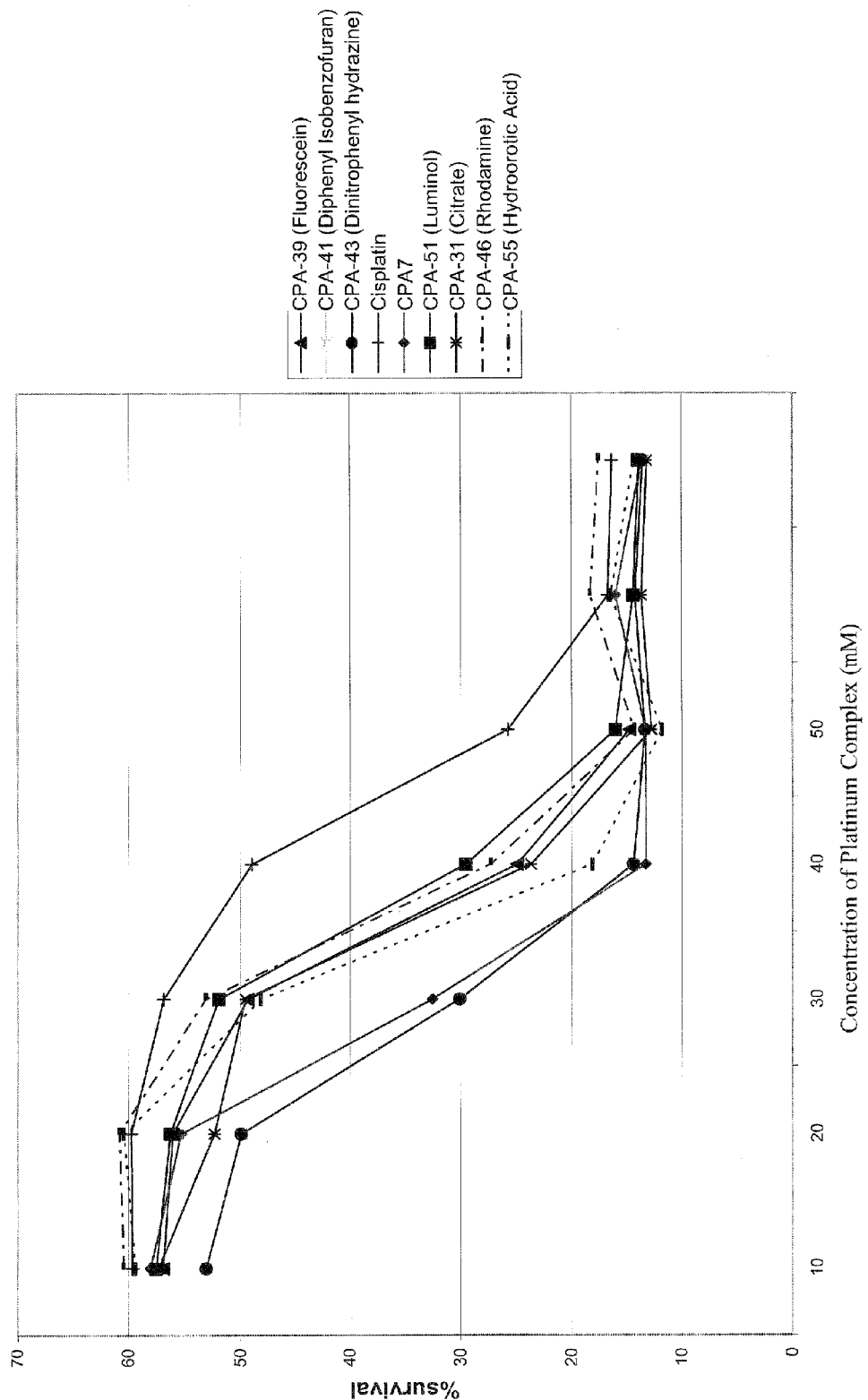
FIG. 3 shows the results in graph form from an XTT assay. Cisplatin is also designated as "Cis-Pt."
Figure 7:
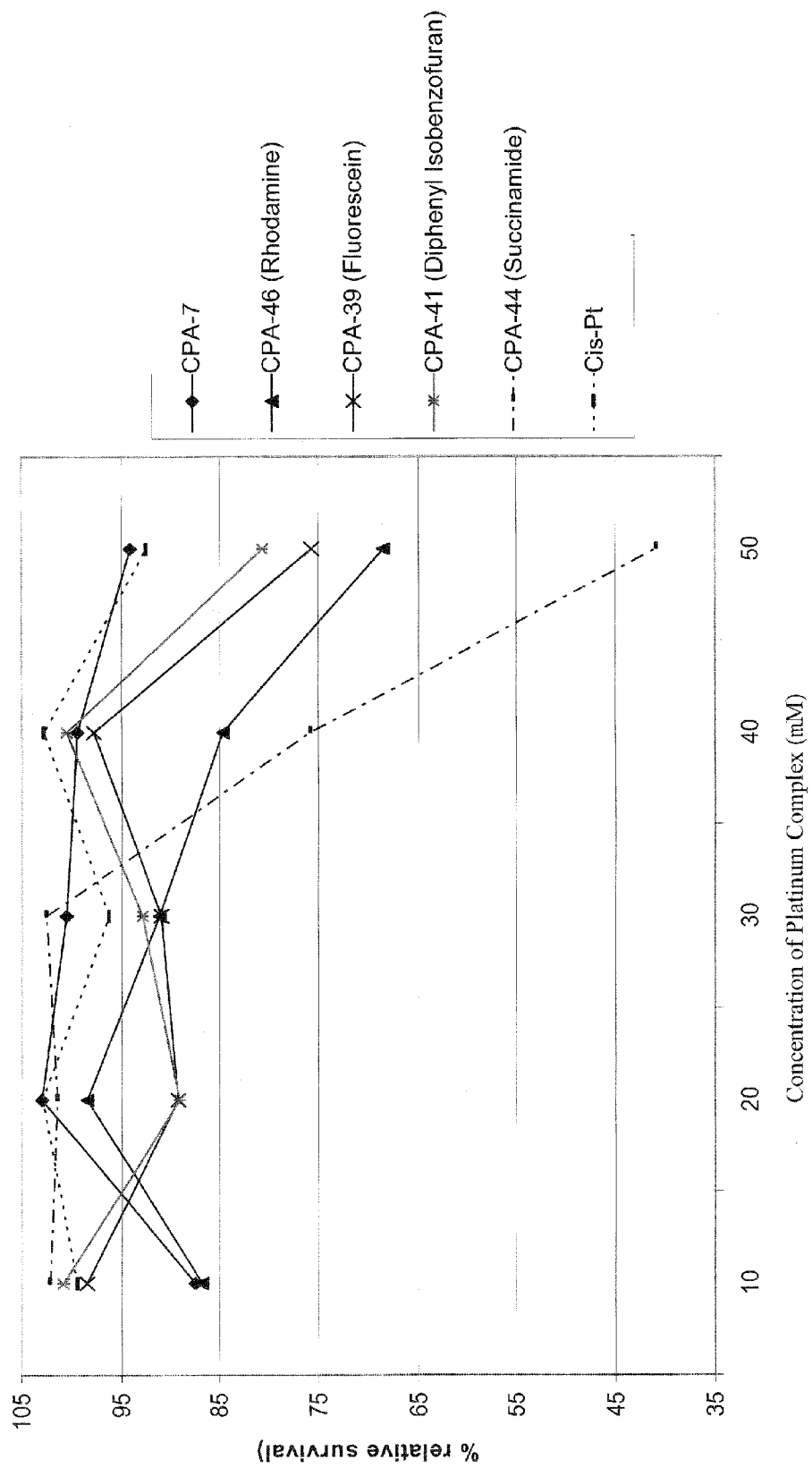
FIG. 7 shows the results in graph form from an XTT assay. Cisplatin is also designated as "Cis-Pt."

The XTT assay is based on the conversion of the yellow tetrazalium salt XTT into an orange formazan dye by metabolically active cells. The orange formazan dye is soluble and can be photometrically quantitated using an ELISA plate reader. A decrease in the number of living cells results in a decrease in total metabolic activity which leads to a decrease in color formation. Platinum complexes of the present invention were tested in XTT assays using A549 cells to determine anti-cancer cell activity. The percent survival of cells versus platinum complex concentration is shown in graphical form in FIGS. 3 and 7.

Example 3

Reduction of CPA-7 Platinum Complex by Glutathione

Figure 5A:
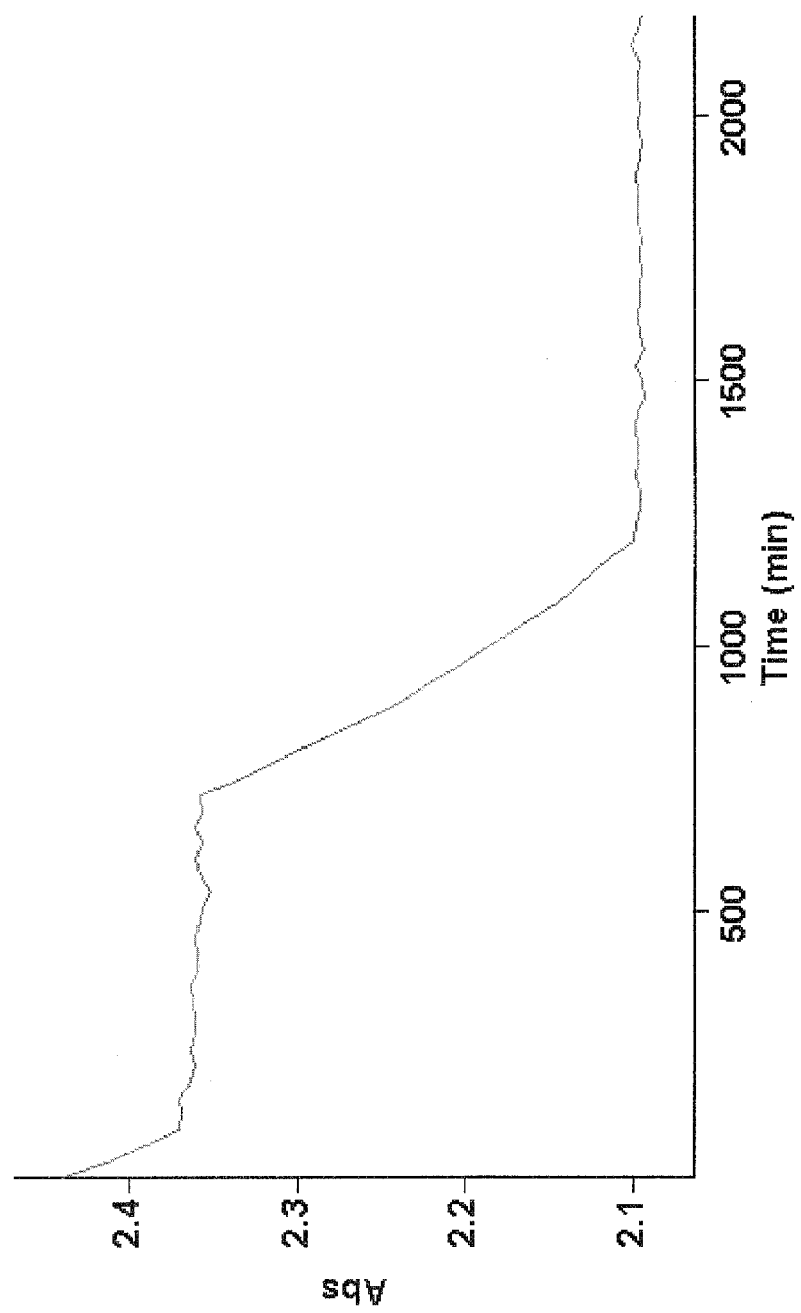
FIGS. 5A-C show inertness of CPA-7 platinum complex to reduction by glutathione. 20 μm CPA-7 in PBS/20% DMSO with 10 mm glutathione.
Figures 5B, 5C:
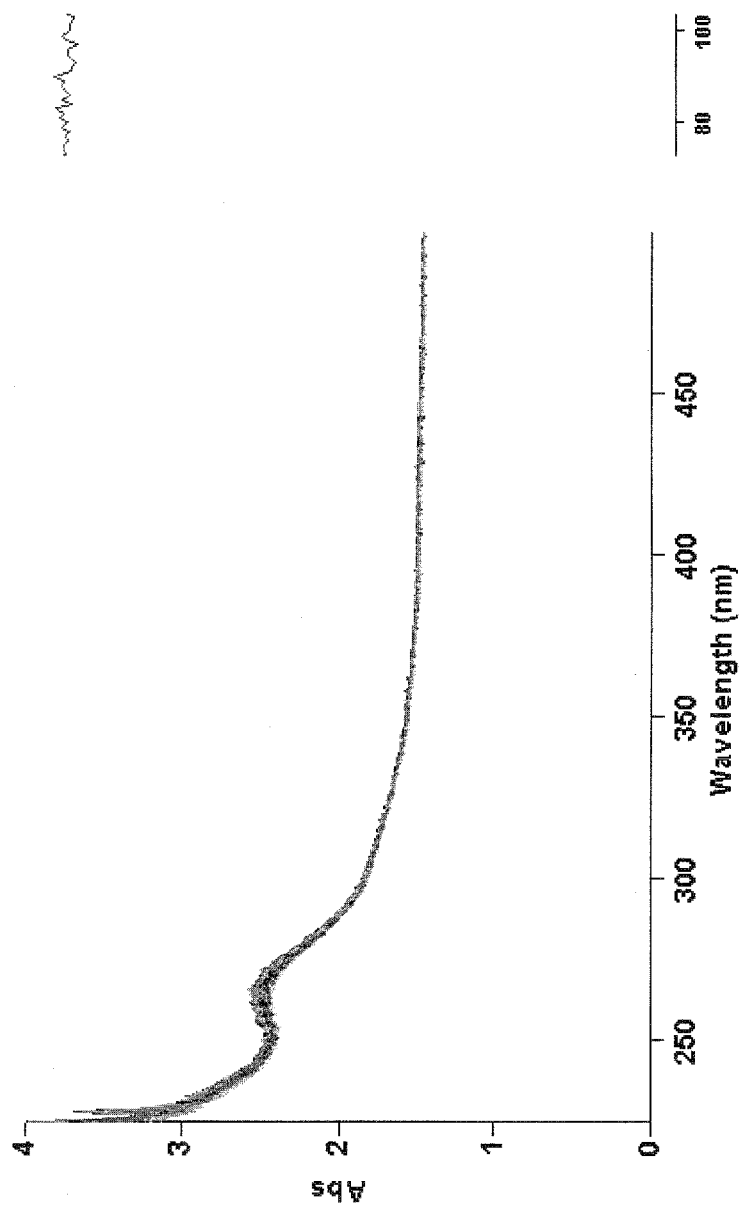

FIGS. 5A-C show the inertness of CPA-7 to glutathione reduction. In the figures, 20 μm CPA-7 was added in PBS/20% DMSO with 10 mM glutathione. The readings were initiated in late evening where data points were collected every 10 minutes at the lambda max for CPA-7, 226 nm. The data shows slow reduction which then virtually stops during the night hours, and resumes the next day. This data demonstrates sensitivity to light and stability against GSH reduction. Data was collected on a Varian Cary 50 fitted with a fibreoptic probe in the kinetics mode. The Cary 50 uses a pulsed Xenon lamp with discontinuous irradiation between readings. A 25-mL volumetric flask was used for the solution with a magnetic stirring bar at slow speed.

Example 4

MTT Assay Data for Platinum Complexes

Figure 8:
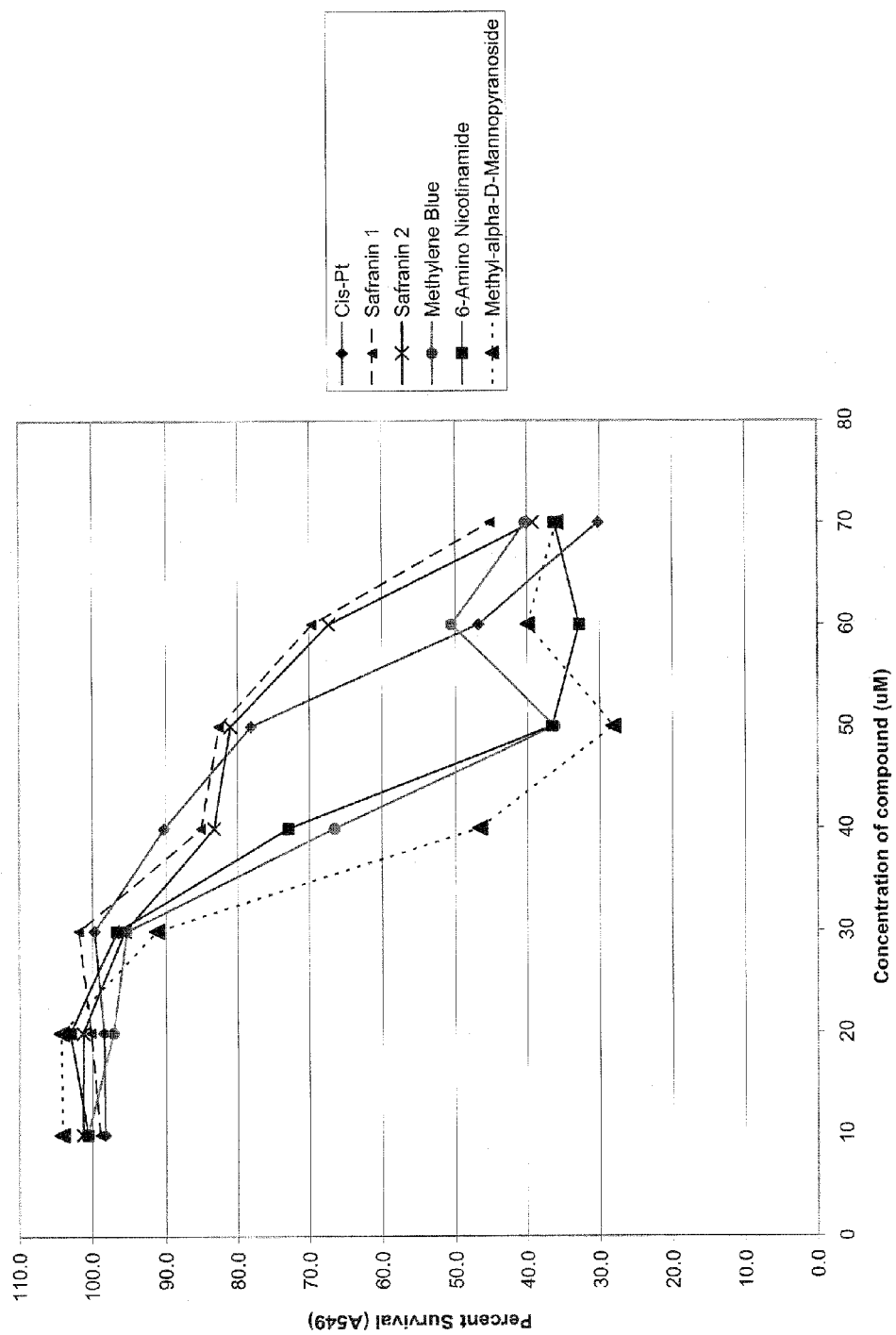
FIG. 8 shows the results in graph form from an MTT assay. The figure legend identifies the $Pt(NO_2)(NH_3)_2(Cl)_2A$ platinum complex by the "A" substituent identified herein. Cisplatin is also designated as "Cis-Pt." Two different isolates of the platinum (IV) complex substituted with Safranin were isolated (referred to herein as Safranin 1 and Safranin 2) and tested in the assay.
Figure 9:
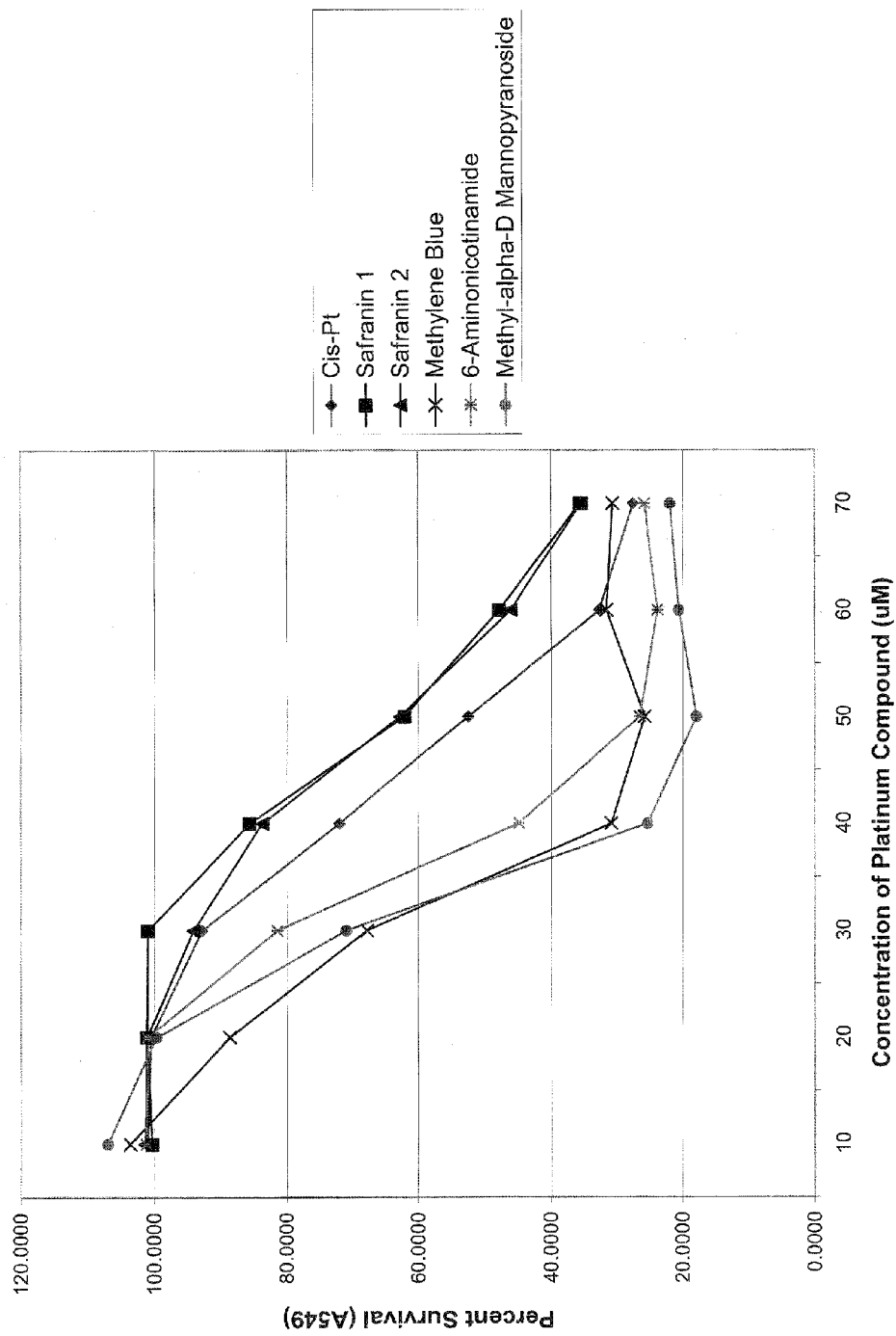
FIG. 9 shows the results in graph form from an MTT assay. The figure legend identifies the $Pt(NO_2)(NH_3)_2(Cl)_2A$ platinum complex by the "A" substituent identified herein. Cisplatin is also designated as "Cis-Pt." Two different isolates of the platinum (IV) complex substituted with Safranin were isolated (referred to herein as Safranin 1 and Safranin 2) and tested in the assay.
Figure 11:
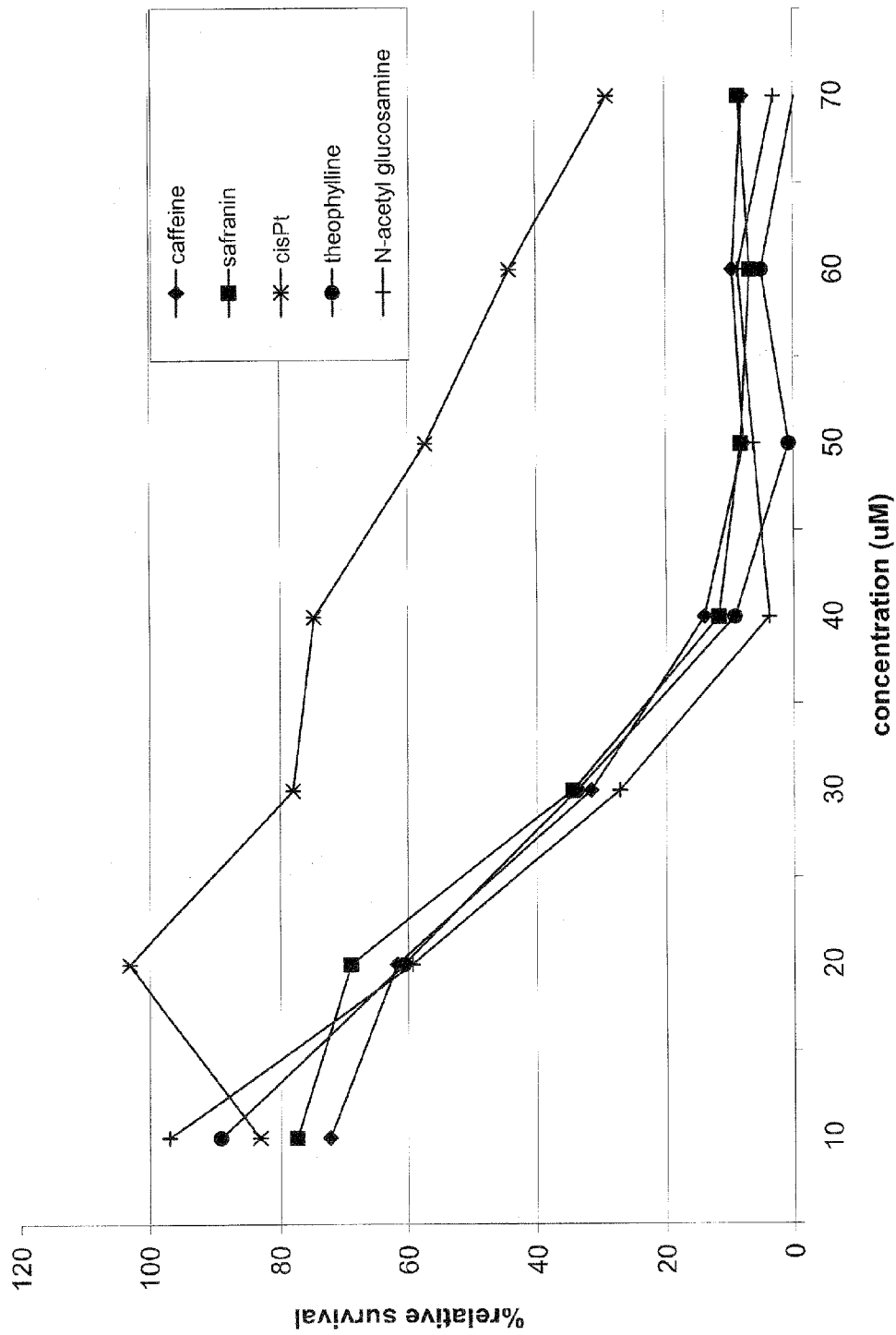
FIG. 11 shows the results in graph form from an MTT assay. The figure legend identifies the $Pt(NO_2)(NH_3)_2(Cl)_2A$ platinum complex by the "A" substituent identified herein. Cisplatin is also designated as "Cis-Pt."

MTT assays are used for the quantitative determination of cellular proliferation and activation and for the quantitation of in vitro tumor cell sensitivity to anti-cancer compounds. The assay is based on the cleavage of the yellow tetrazolium salt MTT into purple colored formazan by metabolically active cells. Solubilized formazan product can be photometrically quantitated using an ELISA plate reader. A decrease in the number of living cells results in a decrease in total metabolic activity which leads to a decrease in color formation. Platinum complexes of the present invention were tested in MTT assays using A549 cells to determine anti-cancer cell activity. The results are shown in Tables 6, 7, 8, and 9 and FIGS. 8, 9, and 11. Table 6 shows percent survival of A549 cells and Table 7 shows the IC50 from the data in Table 6. FIGS. 8, 9, and 11 show percent survival versus platinum complex concentration in graphical form.

TABLE 6

MTT Assay: Percent of Survival of A549 Using cisplatin (Cis-Pt) or a Platinum Complex of formula:

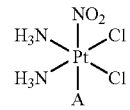

| Complex | Concentration (in μM) | Percent Survival | Average Absorbance |
|---|---|---|---|
| Cis-Pt | 10 | 98.2423 | 2.3196 |
| | 20 | 98.3779 | 2.3228 |
| | 30 | 99.6400 | 2.3526 |
| | 40 | 90.2757 | 2.1315 |
| | 50 | 78.1288 | 1.8447 |
| | 60 | 46.7536 | 1.1039 |
| | 70 | 30.1470 | 0.7118 |
| A = Safranin 1* | 10 | 98.9412 | 2.3361 |
| | 20 | 100.1440 | 2.3645 |
| | 30 | 101.8000 | 2.4036 |
| | 40 | 85.0705 | 2.0086 |
| | 50 | 82.5674 | 1.9495 |
| | 60 | 69.5989 | 1.6433 |
| | 70 | 45.1484 | 1.0660 |
| A = Safranin 2* | 10 | 101.2791 | 2.3913 |
| | 20 | 101.2409 | 2.3904 |
| | 30 | 95.5826 | 2.2568 |
| | 40 | 83.2027 | 1.9645 |
| | 50 | 81.0131 | 1.9128 |
| | 60 | 67.3203 | 1.5895 |
| | 70 | 39.1682 | 0.9248 |
| A = Methylene blue | 10 | 100.5887 | 2.3750 |
| | 20 | 97.1030 | 2.2927 |
| | 30 | 95.3369 | 2.2510 |
| | 40 | 66.5029 | 1.5702 |
| | 50 | 36.1781 | 0.8542 |
| | 60 | 50.4468 | 1.1911 |
| | 70 | 40.2567 | 0.9505 |
| A = 6-Aminonicotinamide | 10 | 100.5548 | 2.3742 |
| | 20 | 103.0071 | 2.4321 |
| | 30 | 96.6245 | 2.2814 |
| | 40 | 72.9025 | 1.7213 |
| | 50 | 36.4999 | 0.8618 |
| | 60 | 32.7771 | 0.7739 |
| | 70 | 36.1526 | 0.8536 |
| A = Methyl alpha-D-Mannopyranoside | 10 | 104.1125 | 2.4582 |
| | 20 | 104.2311 | 2.4610 |
| | 30 | 91.2456 | 2.1544 |
| | 40 | 46.6096 | 1.1005 |
| | 50 | 28.0844 | 0.6631 |
| | 60 | 39.8967 | 0.9420 |
| | 70 | 35.9112 | 0.8479 |

*Two different isolates of the platinum (IV) complex substituted with Safranin were isolated (referred to herein as Safranin 1 and Safranin 2) and tested in the assay.

TABLE 7

Calculated IC50's from MTT Assay Data of Table 1

| Complex | Calculated IC 50 (uM concentration) |
|---|---|
| Safranin 1* | 78.60 |
| Safranin 2* | 72.57 |
| Methylene blue | 56.36 |
| 6-Aminonicotinamide | 53.06 |
| Methyl alpha-D-Mannopyranoside | 50.10 |

Values in bold are outside the measured range. All values are determined using a linear trend from percent survival vs. concentration data.
*Two different isolates of the platinum (IV) complex substituted with Safranin were isolated (referred to herein as Safranin 1 and Safranin 2) and tested in the assay.

TABLE 8

MTT Assay: Percent of Survival of A549 Using cisplatin (Cis-Pt) or a Platinum Complex of formula:

$$\begin{array}{c} NO_2 \\ H_3N\diagdown \mid \diagup Cl \\ Pt \\ H_3N\diagup \mid \diagdown Cl \\ A \end{array}$$

| Complex | Concentration (in μM) | Percent Survival | Average Absorbance |
|---|---|---|---|
| Cis-Pt | 10 | 100.9661 | 2.4665 |
| | 20 | 100.5199 | 2.4556 |
| | 30 | 92.8650 | 2.2686 |
| | 40 | 71.9432 | 1.7575 |
| | 50 | 52.5114 | 1.2828 |
| | 60 | 32.6293 | 0.7971 |
| | 70 | 27.5001 | 0.6718 |
| A = Safranin 1* | 10 | 100.3152 | 2.4506 |
| | 20 | 101.0725 | 2.4691 |
| | 30 | 100.9661 | 2.4665 |
| | 40 | 85.6236 | 2.0917 |
| | 50 | 62.0533 | 1.5159 |
| | 60 | 47.8079 | 1.1679 |
| | 70 | 35.5807 | 0.8692 |
| A = Safranin 2* | 10 | 101.3304 | 2.4754 |
| | 20 | 101.0766 | 2.4692 |
| | 30 | 94.1790 | 2.3007 |
| | 40 | 83.7284 | 2.0454 |
| | 50 | 62.7001 | 1.5317 |
| | 60 | 46.0928 | 1.1260 |
| | 70 | 35.4456 | 0.8659 |
| A = Methylene blue | 10 | 103.5613 | 2.5299 |
| | 20 | 88.6365 | 2.1653 |
| | 30 | 67.6900 | 1.6536 |
| | 40 | 30.7913 | 0.7522 |
| | 50 | 25.7972 | 0.6302 |
| | 60 | 31.5240 | 0.7701 |
| | 70 | 30.6234 | 0.7481 |
| A = 6-Aminonicotinamide | 10 | 101.1544 | 2.4711 |
| | 20 | 100.9947 | 2.4672 |
| | 30 | 81.4442 | 1.9896 |
| | 40 | 44.8770 | 1.0963 |
| | 50 | 26.5463 | 0.6485 |
| | 60 | 23.7873 | 0.5811 |
| | 70 | 25.7645 | 0.6294 |
| A = Methyl alpha-D Mannopyranoside | 10 | 106.9098 | 2.6117 |
| | 20 | 99.6889 | 2.4353 |
| | 30 | 70.8789 | 1.7315 |
| | 40 | 25.2691 | 0.6173 |
| | 50 | 17.8886 | 0.4370 |
| | 60 | 20.5371 | 0.5017 |
| | 70 | 21.8552 | 0.5339 |

*Two different isolates of the platinum (IV) complex substituted with Safranin were isolated (referred to herein as Safranin 1 and Safranin 2) and tested in the assay.

TABLE 9

MTT Assay: Percent of Survival of A549 Using cisplatin (Cis-Pt) or a Platinum Complex of formula:

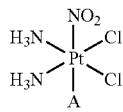

| Complex | Concentration (in μM) | Percent Survival | Average Absorbance |
|---|---|---|---|
| Cis-Pt | 10 | 83.09928 | 0.5299 |
| | 20 | 103.1096 | 0.6575 |
| | 30 | 77.94511 | 0.497033 |
| | 40 | 74.69369 | 0.4763 |
| | 50 | 57.14023 | 0.364367 |
| | 60 | 44.12934 | 0.2814 |
| | 70 | 29.06933 | 0.185367 |
| A = Caffeine | 10 | 72.23683268 | 0.460633333 |
| | 20 | 61.71416504 | 0.393533333 |
| | 30 | 31.61504914 | 0.2016 |
| | 40 | 13.94658583 | 0.088933333 |
| | 50 | 7.814897233 | 0.049833333 |
| | 60 | 9.571288852 | 0.061033333 |
| | 70 | 8.003082049 | 0.051033333 |
| A = Safranin | 10 | 77.35441421 | 0.493266667 |
| | 20 | 68.90177955 | 0.439366667 |
| | 30 | 34.45873081 | 0.219733333 |
| | 40 | 11.68836804 | 0.074533333 |
| | 50 | 8.301041342 | 0.052933333 |
| | 60 | 6.774653387 | 0.0432 |
| | 70 | 8.541499718 | 0.054466667 |
| A = Theophylline | 10 | 89.09505581 | 0.568133333 |
| | 20 | 60.59551085 | 0.3864 |
| | 30 | 33.86281222 | 0.215933333 |
| | 40 | 9.174009795 | 0.0585 |
| | 50 | 0.737057197 | 0.0047 |
| | 60 | 4.97644292 | 0.031733333 |
| | 70 | −0.245685732 | −0.001566667 |
| A = N-acetyl glucosamine | 10 | 96.89427097 | 0.617866667 |
| | 20 | 59.27298978 | 0.377966667 |
| | 30 | 27.21361538 | 0.173533333 |
| | 40 | 3.75846897 | 0.023966667 |
| | 50 | 6.225781006 | 0.0397 |
| | 60 | 8.661728906 | 0.055233333 |
| | 70 | 2.974365569 | 0.018966667 |

Example 5

XTT Assay Data for Platinum Complexes

Figure 10:
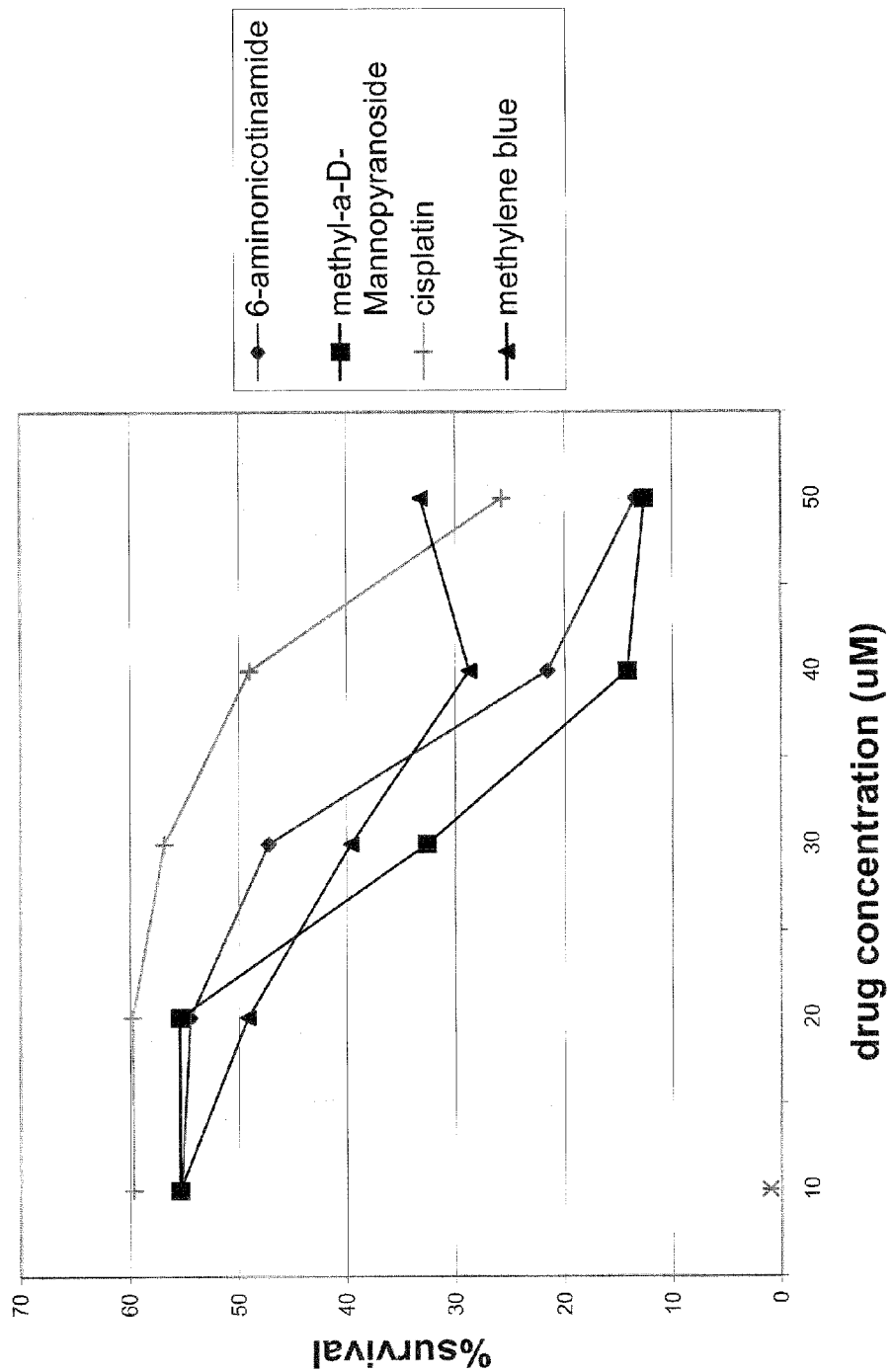
FIG. 10 shows the results in graph form from an XTT assay. The figure legend identifies the $Pt(NO_2)(NH_3)_2(Cl)_2A$ platinum complex by the "A" substituent identified herein.

The XTT assay is based on the conversion of the yellow tetrazalium salt XTT into an orange formazan dye by metabolically active cells. The orange formazan dye is soluble and can be photometrically quantitated using an ELISA plate reader. A decrease in the number of living cells results in a decrease in total metabolic activity which leads to a decrease in color formation. Platinum complexes of the present invention were tested in XTT assays using A549 cells to determine anti-cancer cell activity. The percent survival of cells versus platinum complex concentration is shown in graphical form in FIG. 10.

Example 6

Inhibition of In Vitro Stat3 DNA-Binding Activity by HK-Designated Platinum complexes Other platinum (IV) complexes were evaluated for inhibitory activity against STAT DNA-binding in vitro. Analysis by EMSA of nuclear extracts prepared from EGF-stimulated fibroblast that activates Stat1, Stat3 and Stat5 shows that preincubation (of extracts of equal total protein) with different concentrations of platinum complexes for 30 min prior to incubation with $^{32}$P-labeled hSIE probe results in a dose-dependent reduction in the levels of DNA-binding activities of Stat3 and Stat1 (FIGS. 12A and 12B).

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

Published U.S. Patent Application No. 20030032594
Published U.S. Patent Application No. 20020120100
Published U.S. Patent Application No. 20020035243
Akira, S. (2000) "Roles of STAT3 defined by tissue-specific gene targeting" *Oncogene* 19:2607-2611.
Ardizzoni, A., Antonelli, G., Grossi, F., Tixi, L., Cafferata, M., Rosso, R. (1999) "The combination of etoposide and cisplatin in non-small-cell lung cancer (NSCLC)" *Ann. Oncol.* 10:S13-17.
Bowman, T., Garcia, R., Turkson, J., Jove, R. (2000) "STATs in oncogenesis" *Oncogene* 19:2474-2488.

Bromberg, J. F., Horvath, C. M., Wen, Z., Schreiber, R. D., Darnell, J. E., Jr. (1996) "Transcriptionally active Stat1 is required for the antiproliferative effects of both interferon alpha and interferon gamma" *Proc. Natl. Acad. Sci. USA* 93:7673-7678.

Bromberg, J. F., Horvath, C. M., Besser, D., Lathem, W. W., Darnell, J. E., Jr. (1998) "Stat3 activation is required for cellular transformation by v-src" *Mol. Cell. Biol.* 18:2553-2558.

Bromberg, J. F., Wrzeszczynska, M. H., Devgan, G., Zhao, Y., Pestell, R. G., Albanese, C., Darnell, J. E., Jr. (1999) "Stat3 as an oneogene" *Cell* 98:295-303.

Catlett-Falcone, R., Landowski, T. H., Oshiro, M. M., Turkson, J., Levitzki, A., Savino, R., Ciliberto, G., Moscinski, L., Fernandez-Luna, J. L., Nunez, G., Dalton, W. S., Jove, R. (1999a) "Constitutive activation of Stat3 signaling confers resistance to apoptosis in human U266 myeloma cells" *Immunity* 10:105-115.

Catlett-Falcone, R., Dalton, W. S., Jove, R. (1999b) "STAT proteins as novel targets for cancer therapy. Signal transducer an activator of transcription" *Curr. Opin. Oncol.* 11:490-496.

Coffer, P. J., Koenderman, L., de Groot, R. P. (2000) "The role of STATs in myeloid differentiation and leukemia" *Oncogene* 19:2511-2522.

Cuny, G. D. et al. (1999) "Photoactivated virucidal properties of tridentate 2,2'-dihydroxyazobenzene and 2-salicylideneaminophenol platinum pyridine complexes" *Bioorganic and Medicinal Chemistry Letters* 9(2):237-240.

Darnell, J. E., Jr., Kerr, I. M., Stark, G. R. (1994) "Jak-STAT pathways and transcriptional activation in response to IFNs and other extracellular signaling proteins" *Science* 264:1415-1421.

Darnell, J. E., Jr. (1997) "STATs and Gene Regulation" *Science* 277:1630-1635.

Epling-Burnette, P. K., Lui, J. H., Catlette-Falcone, R., Turkson, J., Oshiro, M., Kothapalli, R., Li, Y., Wang, J.-M., Yang-Yen, H.-F., Karras, J., Jove, R., Loughran, T. P., Jr. (2001) "Inhibition of STAT3 signaling leads to apoptosis of leukemic large granular lymphocytes and decreased Mcl-1 expression" *J. Clin. Invest* 107:351-362.

Fukada, T., Hibi, M., Yamanaka, Y., Takahashi-Tezuka, M., Fujitani, Y., Yamaguchi, T., Nakajima, K., Hirano, T. (1996) "Two signals are necessary for cell proliferation induced by a cytokine receptor gp130: involvement of STAT3 in anti-apoptosis" *Immunity* 5:449-460.

Garcia, R., Jove, R. (1998) "Activation of STAT transcription factors in oncogenic tyrosine kinase signaling" *J. Biomed. Sci.* 5:79-85.

Garcia, R., Bowman, T. L., Niu, G., Yu, H., Minton, S., Muro-Cacho, C. A., Cox, C. E., Falcone, R., Fairclough, R., Parson, S., Laudano, A., Gazit, A., Levitzki, A., Kraker, A., Jove, R. (2001) "Constitutive activation of Stat3 by the Src and JAK tyrosine kinases participates in growth regulation of human breast carcinoma cells" *Oncogene* 20:2499-2513.

Grandis, J. R., Drenning, S. D., Chakraborty, A., Zhou, M. Y., Zeng, Q., Pitt, A. S., Tweardy, D. J. (1998) "Requirement of Stat3 but not Stat1 activation for epidermal growth factor receptor-mediated cell growth In vitro" *J. Clin. Invest.* 102:1385-1392.

Grandis, J. R., Drenning, S. D., Zeng, Q., Watkins, S. C., Melhem, M. F., Endo, S., Johnson, D. E., Huang, L., He, Y., Kim, J. D. (2000) "Constitutive activation of Stat3 signaling abrogates apoptosis in squamous cell carcinogenesis in vivo" *Proc. Natl. Acad. Sci. USA* 97:4227-4232.

Hirano, T., Ishihara, K., Hibi, M. (2000) "Roles of STAT3 in mediating the cell growth, differentiation and survival signals relayed through the IL-6 family of cytokine receptors" *Oncogene* 19:2548-2556.

Kotenko, S. V., Pestka, S. (2000) "Jak-Stat signal transduction pathway through the eyes of cytokine class II receptor complexes" *Oncogene* 19:2557-2565.

Lin, T. S., Mahajan, S., Frank, D. A. (2000) "STAT signaling in the pathogenesis and treatment of leukemias" *Oncogene* 19:2496-2504.

Nielsen, M., Kaltoft, K., Nordahl, M., Ropke, C., Geisler, C., Mustelin, T., Dobson, P., Svejgaard, A., Odum, N. (1997) "Constitutive activation of a slowly migrating isoform of Stat3 in mycosis fungoides: tyrphostin AG490 inhibits Stat3 activation and growth of mycosis fungoides tumor cell lines" *Proc. Natl. Acad. Sci. USA* 94:6764-6769.

Nielsen, M., Kaestel, C. G., Eriksen, K. W., Woetmann, A., Stokkedal, T., Kaltoft, K., Geisler, C., Ropke, C., Odum, N. (1999) "Inhibition of constitutively activated Stat3 correlates with altered Bcl-2/Bax expression and induction of apoptosis in mycosis fingoides tumor cells" *Leukemia* 13:735-738.

Nitiss, J. L. (2002) "A copper connection to the uptake of platinum anticancer drugs" *Proc. Natl. Acad. Sci. USA* 99:13963-13965.

Persons, D. L., Yazlovitskaya, E. M., Cui, W., Pelling, J. C. (1999) "Cisplatin-induced Activation of Mitogen-activated Protein Kinases in Ovarian Carcinoma Cells: Inhibition of Extracellular Signal-regulated Kinase Activity Increases Sensitivity to Cisplatin" *Clin. Cancer Res.* 5:1007-1014.

Sanchez-Perez, I., Murguia, J. R., Perona, R. (1998) "Cisplatin induces a persistent activation of JNK that is related to cell death" *Oncogene* 16:533-540.

Schindler, C., Darnell, J. E., Jr. (1995) "Transcriptional responses to polypeptide ligands: the JAK-STAT pathway" *Annu. Rev. Biochem.* 64:621-651.

Smithgall, T. E., Briggs, S. D., Schreiner, S., Lerner, E. C., Cheng, H., Wilson, M. B. (2000) "Control of myeloid differentiation and survival by Stats" *Oncogene* 19:2612-2618.

Song, J. I., Grandis, J. R. (2000) "STAT signaling in head and neck cancer" *Oncogene* 19:2489-2495.

Stark, G. R., Kerr, I. M., Williams, B. R., Silverman, R. H., Schreiber, R. D. (1998) "How cells respond to interferons" *Annu. Rev. Biochem.* 67:227-264.

Toyoizumi, T., R. Mick, A. E. Abbas, E. H. Kang, L. R. Kaiser, K. L. Molnar-Kimber (1999) "Combined therapy with chemotherapeutic agents and herpes simplex virus type IICP34.5 mutant (HSV-1716) in human non-small cell lung cancer" *Human Gene Therapy* 10(18):17.

Turkson, J., Bowman, T., Garcia, R., Caldenhoven, E., de Groot, R. P., Jove, R. (1998) "Stat3 activation by Src induces specific gene regulation and is required for cell transformation" *Mol. Cell. Biol.* 18:2545-2552.

Turkson, J., Jove, R. (2000) "STAT proteins: novel molecular targets for cancer drug discovery" *Oncogene* 19:6613-6626.

---

We claim:

1. A method for synthesis of a platinum complex, said method comprising:
   a) mixing cisplatin in water and an organic solvent;
   b) mixing into the mixture of step (a) a ligand capable of bonding to the platinum of cisplatin to form the platinum complex product;
   c) contacting the mixture of step (b) with nitrogen dioxide gas; and
   d) separating the platinum complex product from the solvent.

2. The method according to claim 1, wherein the organic solvent is dichloroethane or hexane.

3. The method according to claim 1, wherein the platinum complex product is separated from the solvent by evaporation of the solvent.

4. The method according to claim 1, wherein following step (d), the platinum complex product is further purified.

5. The method according to claim 4, wherein the platinum complex product is further purified by recrystallization in a solvent.

6. The method according to claim 4, wherein the platinum complex product is further purified by adsorption on a silica column or by high performance liquid chromatography (HPLC).

7. The method according to claim 1, wherein the platinum complex has the structure shown in formula I:

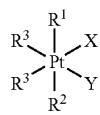
(I)

wherein

X and Y are, independently, any halogen, —NO$_2$, —ONO, or the structure:

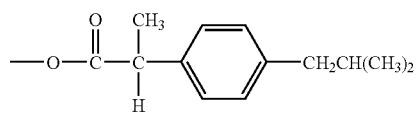

or X and Y together form the structure:

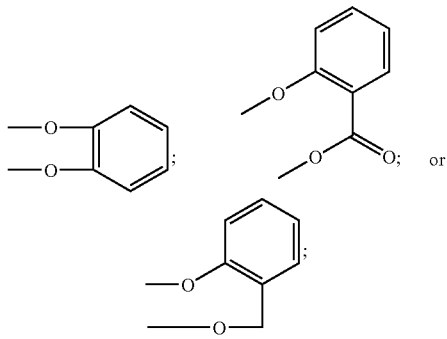

$R^1$ is —NO$_2$ or —ONO;

$R^2$ is any halogen, —OH, —ONO, —ONO$_2$, —COR$^{10}$, —OPO$_3$R$^{10}$R$^{11}$, —OSO$_3$H, —OSeOOH, —SeOOH, —AsO$_2$, —OAsO$_2$, —NR$^{10}$R$^{11}$, —NHR$^{10}$R$^{11}$, —OOCR$^{15}$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —NO$_2$, —NH$_2$, —N-alkyl, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, or the structure:

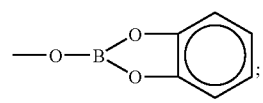

any of which can be substituted with any halogen, —NH$_2$, —COOH, —OH, alkoxy, cycloalkoxy;

$R^3$ is, independently, —NH$_3$, or —NHR$^7$;

$R^7$ is H, C$_{1-6}$ alkyl, alkoxy, or aryl, optionally substituted with —NO$_2$ or —COOH;

$R^{10}$ and $R^{11}$ are, independently, H, —NH$_2$, —OH, —NHR$^7$, CONHR$^7$, CON(R$^7$), C$_{1-6}$ alkyl, aryl, or heteroaryl, any of which can be optionally substituted with any halogen, —COOH, —OH, —NO$_2$, —NH$_2$, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{15}$ is alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with any halogen, —COOH, —OH, —NO$_2$, —NH$_2$, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

or a pharmaceutically acceptable salt thereof.

8. The method according to claim 7, wherein X and Y are, independently, selected from the group consisting of F, Cl, Br, and I.

9. The method according to claim 7, wherein X and Y are both Cl.

10. The method according to claim 7, wherein $R^1$ is —NO$_2$.

11. The method according to claim 7, wherein $R^3$ is —NH$_3$.

12. The method according to claim 1, wherein the platinum complex has the structure shown in formula III or formula IV:

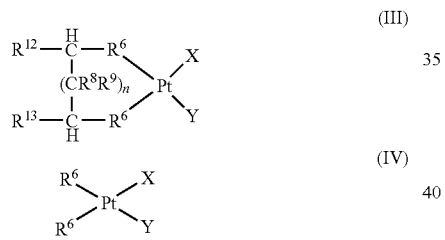

wherein

X and Y are, independently, any halogen, —NO$_2$, —ONO, or X and Y together form the structure:

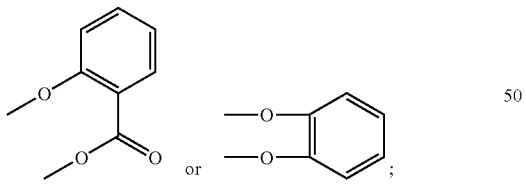

$R^6$ is, independently, NO$_2$, N, NH, or NH$_2$;

$R^8$ and $R^9$ are, independently, H, $C_{1-6}$ alkyl, or —OH, any of which can be optionally substituted with any halogen, —COOH, —OH, —NO$_2$, —NH$_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

$R^{12}$ and $R^{13}$ are, independently, H or $C_{1-6}$ alkyl, or $R^{12}$ and $R^{13}$ together form an aryl, cycloalkyl, heterocycloalkyl, or heteroaryl, any of which can be optionally substituted with any halogen, —COOH, —OH, —NO$_2$, —NH$_2$, alkyl, alkoxy, cycloalkyl, cycloalkoxy, aryl, aryloxy, alkycarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

n is any integer from 0 to 6;

or a pharmaceutically acceptable salt thereof.

13. The method according to claim 1, wherein the platinum complex has the structure shown in formula V or formula VI:

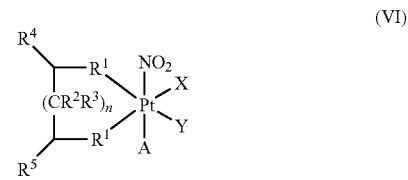

wherein

X and Y are, independently, any halogen, —OH, H$_2$O, or —SO(CH$_3$)$_2$;

and A can be any of the following:

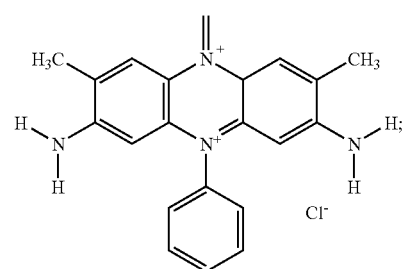

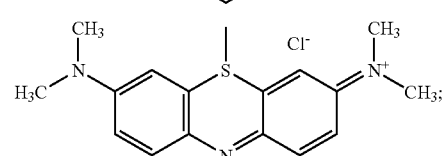

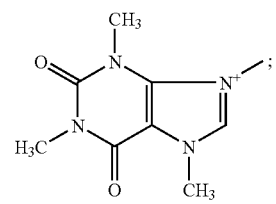

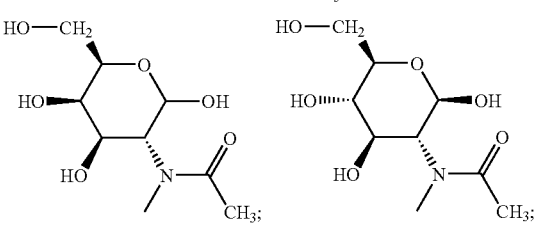

-continued

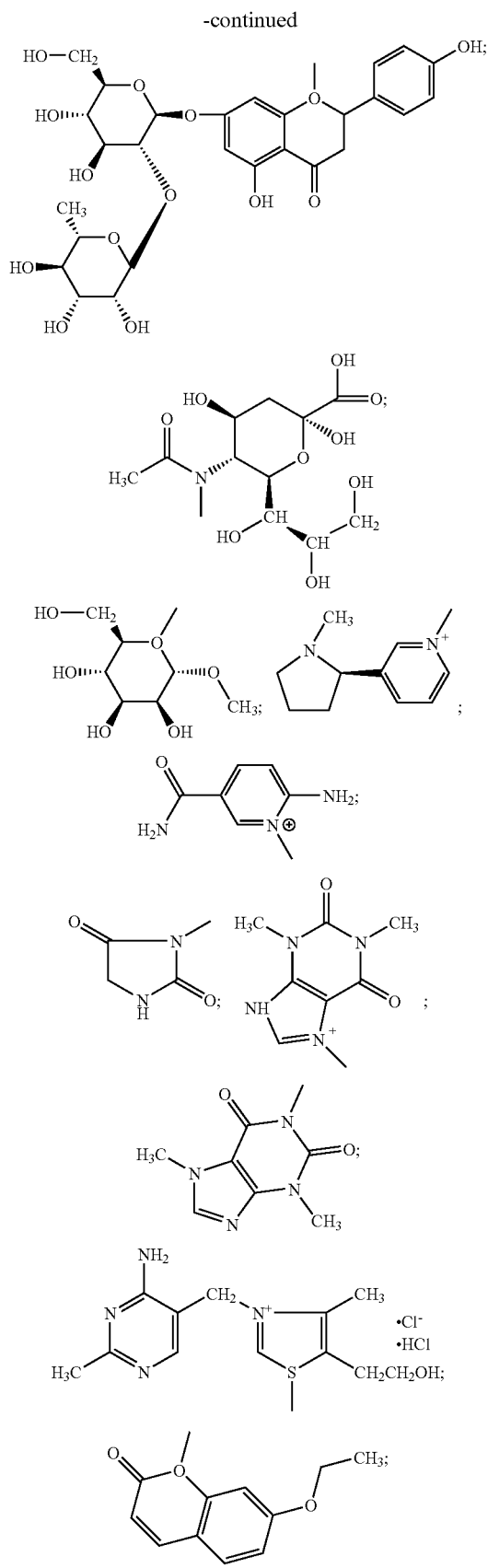

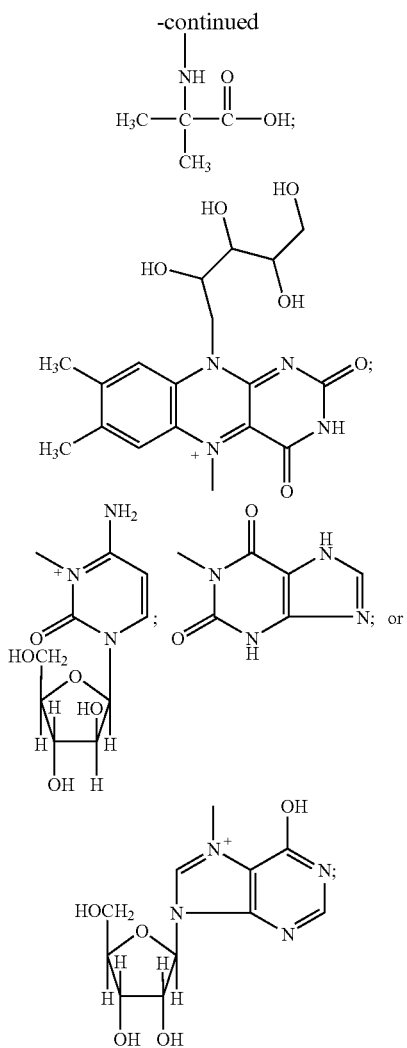

and wherein $R^1$ is, independently, $NH_2$ or NH;

$R^2$ and $R^3$ are, independently, H, —OH, $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, and heteroarylcarbonyl;

$R^4$ and $R^5$ are, independently, H or $C_{1-6}$ alkyl, alkoxy, cycloalkyl, aryloxy, cycloalkoxy, aryl, heteroalkyl, heterocycloalkyl, heteroaryl, arylcarbonyl, and heteroarylcarbonyl or $R^4$ and $R^5$ together form a cycloalkyl, cycloalkoxy, aryl, aryloxy, heterocycloalkyl, heteroaryl, arylcarbonyl, and heteroarylcarbonyl, any of which can be optionally substituted with alkyl, alkoxy, cycloalkyl, aryloxy, cycloalkoxy, aryl, heteroalkyl, heterocycloalkyl, heteroaryl, arylcarbonyl, and heteroarylcarbonyl;

n is any integer from 0 to 6;

or a pharmaceutically acceptable salt thereof.

14. The method according to claim 13, wherein X and Y are, independently, selected from the group consisting of F, Cl, Br, and I.

15. The method according to claim 13, wherein X and Y are both Cl.
16. The method according to claim 13, wherein the platinum complex is selected from the group consisting of
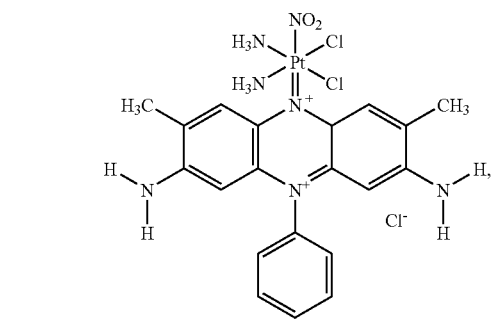
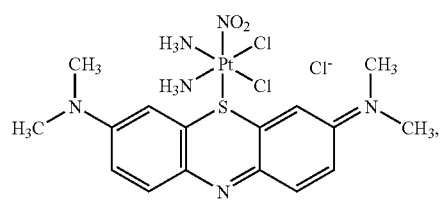
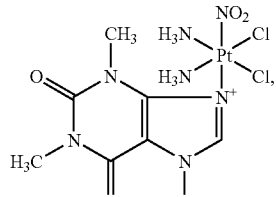
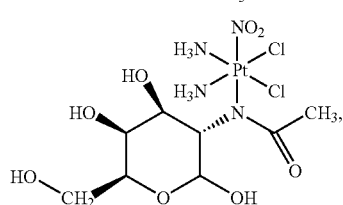
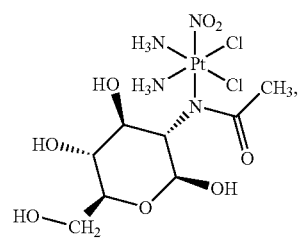
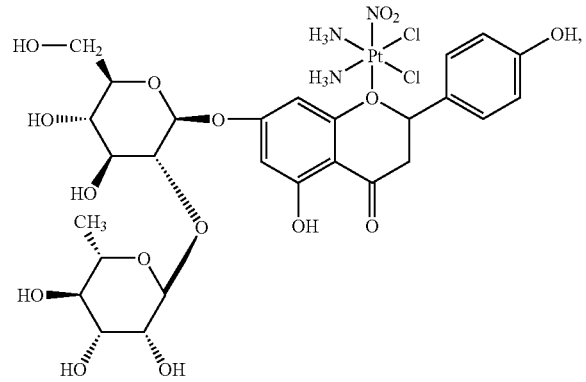
-continued
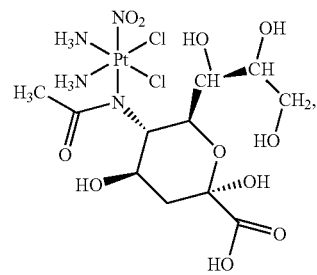
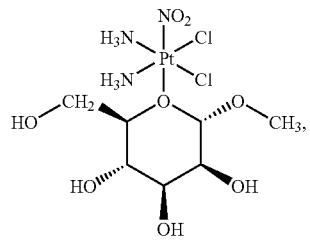
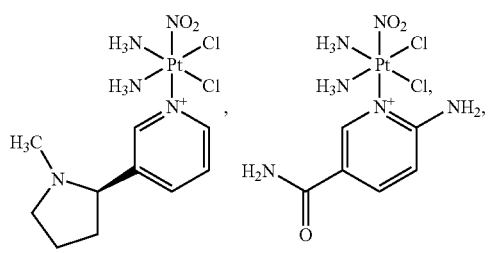
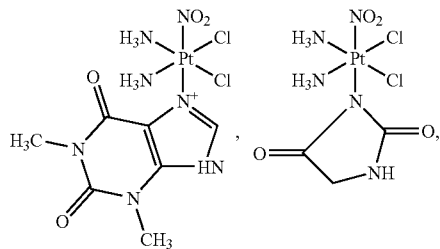
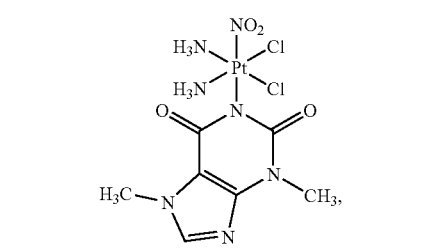
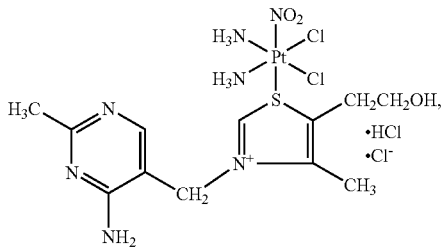

-continued
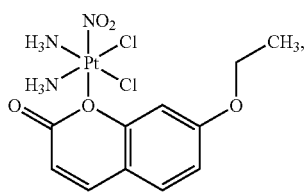
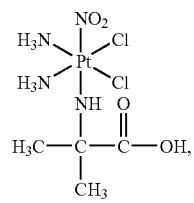
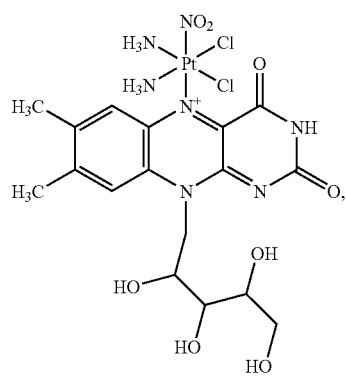
-continued
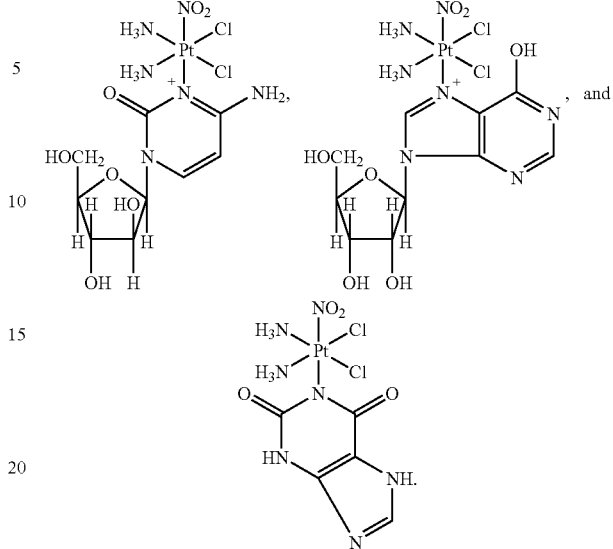
17. The method according to claim 1, wherein the platinum complex has the structure:
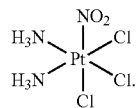
* * * * *

UNITED STATES PATENT AND TRADEMARK OFFICE
CERTIFICATE OF CORRECTION

Page 1 of 3

PATENT NO. : 7,759,510 B2
APPLICATION NO. : 12/506913
DATED : July 20, 2010
INVENTOR(S) : Heidi Kay et al.

It is certified that error appears in the above-identified patent and that said Letters Patent is hereby corrected as shown below:

Column 5,
Line 40, "SeOOH" should read -- -SeOOH --.

Column 10,
Line 54 (cytarabine),

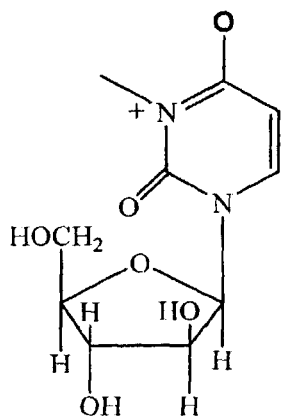

"   (cytarabine)   " should read --

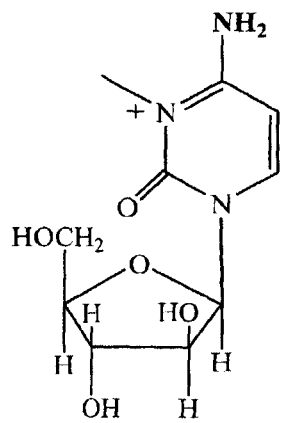

(cytarabine)   --.

Signed and Sealed this
Fourth Day of January, 2011

David J. Kappos
*Director of the United States Patent and Trademark Office*

CERTIFICATE OF CORRECTION (continued)
U.S. Pat. No. 7,759,510 B2

Column 10,
Line 55 (xanthine),

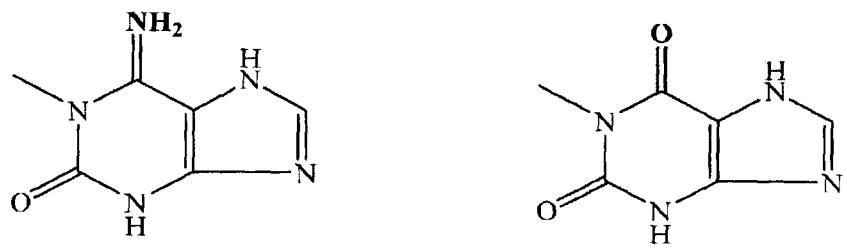

"      (xanthine)      " should read --      (xanthine)      --.

Column 18,
Line 4, "475 mm" should read --475 nm--.

Column 22,
Line 20 (CPA-9),

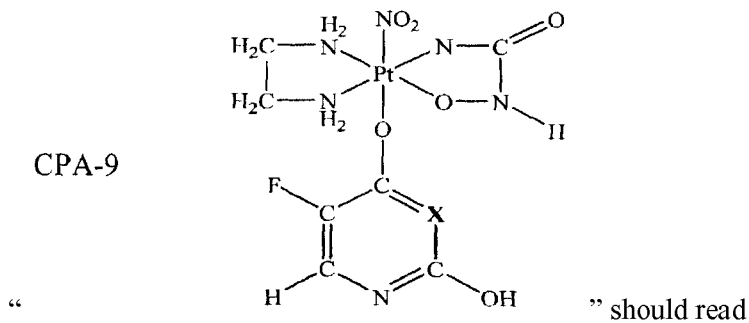

"         " should read

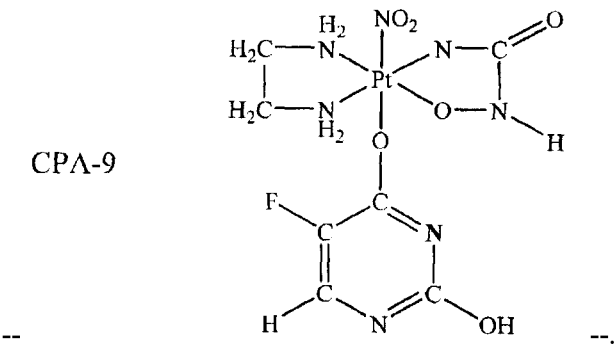

--         --.

CERTIFICATE OF CORRECTION (continued)  
U.S. Pat. No. 7,759,510 B2

Page 3 of 3

Column 45,
Line 23,

" 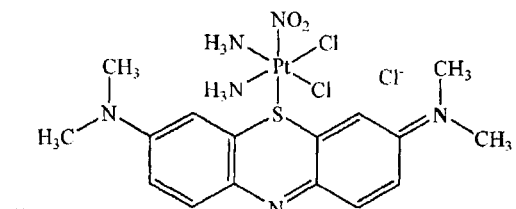                                    " should read

-- 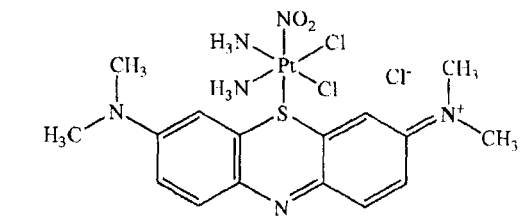                                    --.